US011655454B1

(12) United States Patent
Donner et al.

(10) Patent No.: US 11,655,454 B1
(45) Date of Patent: May 23, 2023

(54) METHOD AND APPARATUS FOR IMPROVED MESENCHYMAL STEM CELL HARVESTING

(71) Applicant: Elite IP, LLC, Johnstown, CO (US)

(72) Inventors: Edward Jeffrey Donner, Fort Collins, CO (US); Christopher Thomas Donner, Fort Collins, CO (US); Ryan Dregalla, Lyons, CO (US); Lucanus Steven Koldewyn, Johnstown, CO (US)

(73) Assignee: Elite IP, LLC, Johnstown, CO (US)

( * ) Notice: Subject to any disclaimer, the term of this patent is extended or adjusted under 35 U.S.C. 154(b) by 1018 days.

(21) Appl. No.: 15/933,314

(22) Filed: Mar. 22, 2018

Related U.S. Application Data

(60) Provisional application No. 62/475,753, filed on Mar. 23, 2017.

(51) Int. Cl.
*C12N 5/0775* (2010.01)
*A61K 35/28* (2015.01)

(52) U.S. Cl.
CPC ............ *C12N 5/0663* (2013.01); *A61K 35/28* (2013.01); *C12N 2509/10* (2013.01); *C12N 2527/00* (2013.01)

(58) Field of Classification Search
CPC .............. C12N 5/0663; C12N 2509/10; C12N 2527/00; A61K 35/28
See application file for complete search history.

(56) References Cited

U.S. PATENT DOCUMENTS

| | | | | |
|---|---|---|---|---|
| 4,895,146 A | * | 1/1990 | Draenert | B28D 1/041 606/180 |
| 5,824,084 A | * | 10/1998 | Muschler | A61L 27/32 128/898 |
| 5,908,784 A | * | 6/1999 | Johnstone | C12N 5/0655 435/395 |
| 8,460,860 B2 | * | 6/2013 | Williams | A61L 27/3683 435/1.3 |
| 2015/0342756 A1 | * | 12/2015 | Bays | A61F 2/4644 604/22 |
| 2016/0151537 A1 | * | 6/2016 | Govil | A61L 27/56 424/549 |

FOREIGN PATENT DOCUMENTS

WO WO-9716118 A1 * 5/1997 .......... A61B 10/025

OTHER PUBLICATIONS

Zhou BO, Yue R, Murphy MM, Peyer JG, Morrison SJ. Leptin-receptor-expressing mesenchymal stromal cells represent the main source of bone formed by adult bone marrow. Cell Stem Cell. Aug. 7, 2014;15(2):154-68. doi: 10.1016/j.stem.2014.06.008. Epub Jun. 19, 2014. PMID: 24953181; PMCID: PMC4127103. (Year: 2014).*
Sakaguchi Y, Sekiya I, Yagishita K, Ichinose S, Shinomiya K, Muneta T. Suspended cells from trabecular bone by collagenase digestion become virtually identical to mesenchymal stem cells obtained from marrow aspirates. Blood. Nov. 1, 2004;104(9):2728-35. (Year: 2004).*
Uccelli A, Moretta L, Pistoia V. Mesenchymal stem cells in health and disease. Nat Rev Immunol. Sep. 2008;8(9):726-36. (Year: 2008).*
Lee S, Choi E, Cha MJ, Hwang KC. Cell adhesion and long-term survival of transplanted mesenchymal stem cells: a prerequisite for cell therapy. Oxid Med Cell Longev. 2015;2015:632902. (Year: 2015).*
Spooncer et al. "Regulation of haemopoiesis in long-term bone marrow cultures. IV. Glycosaminoglycan synthesis and the stimulation of haemopoiesis by beta-D-xylosides" J Cell Biol. Feb. 1, 1983; 96(2): 510-514. (Year: 1983).*
Aggarwal et al."Human mesenchymal stem cells modulate allogeneic immune cell response" Blood. Feb. 15, 2005;105(4):1815-22. (Year: 2005).*
Anthony et al. "Regulation of Hematopoietic Stem Cells by Bone Marrow Stromal Cells." Trends Immunol. Jan. 2014; 35(1): 32-37. (Year: 2013).*

* cited by examiner

*Primary Examiner* — Titilayo Moloye
(74) *Attorney, Agent, or Firm* — Glenn H. Lenzen; Elevated IP, LLC

(57) ABSTRACT

A mesenchymal stem cell harvesting system and method for increasing the efficiency of collecting and processing physiological fluids containing mesenchymal stem cells from a cavity within a patient's skeletal system. Microenvironments risk in MSC production and concentration within a cavity, for example the patient's ilium, are penetrated with a pointed instrument used to create an aperture in the hard cortical bone forming the cavity followed by the insertion of an aspiration device which extracts one or more samples of cancellous bone, bone marrow, bone marrow blood and other aspirated material. The aspirate is rinsed and may be filtered to remove unwanted material and to increase the concentration and purity of the mesenchymal stem cells in the aspirant far beyond levels formerly obtainable for use in autologous treatment of the patient.

4 Claims, 35 Drawing Sheets

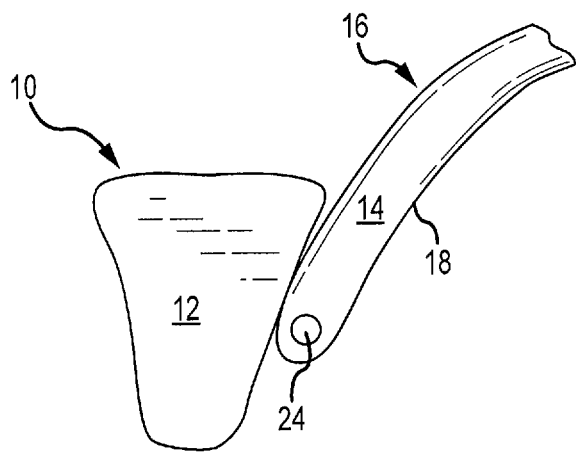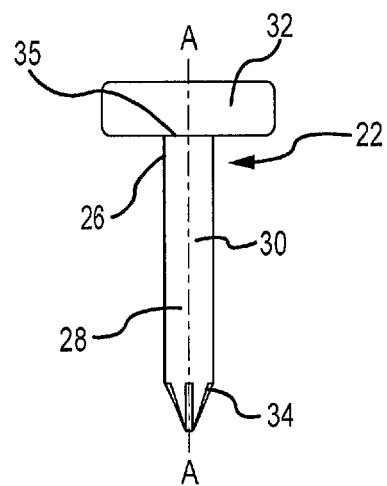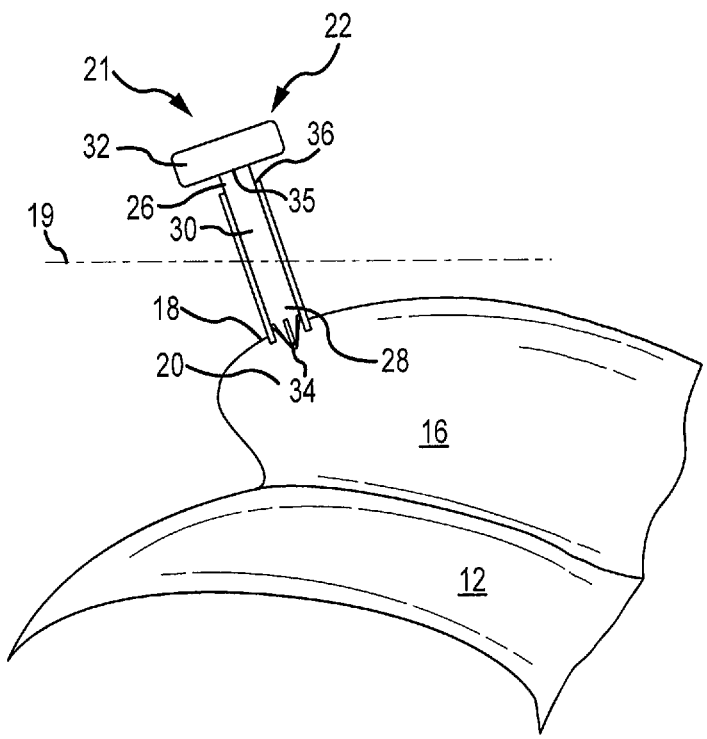
FIG.1A
FIG.1B
FIG.1C

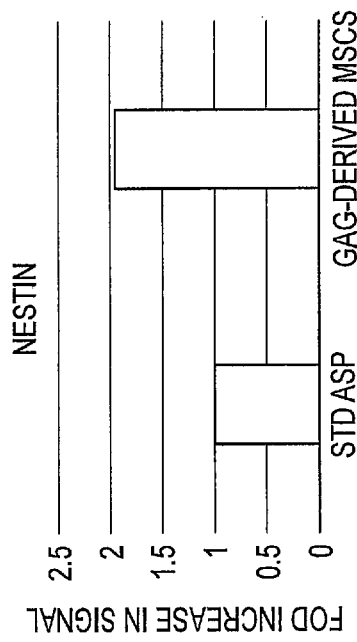
FIG.34B
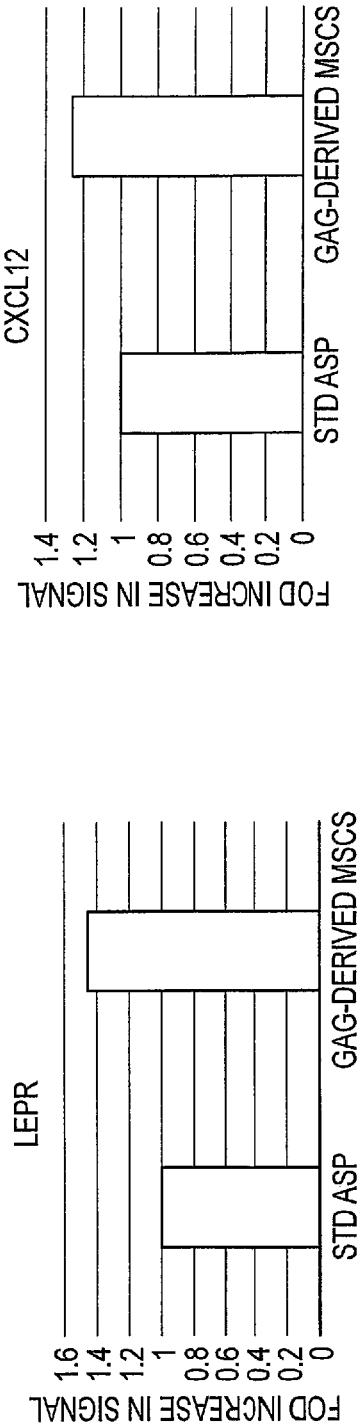
FIG.34C
FIG.34A

METHOD AND APPARATUS FOR IMPROVED MESENCHYMAL STEM CELL HARVESTING

CROSS REFERENCE TO RELATED APPLICATIONS

This application claims the benefit of U.S. Provisional Application No. 62/475,753, filed Mar. 23, 2017, the entire disclosure of which is incorporated herein by reference.

FIELD OF THE INVENTION

The present invention relates generally to the field of medical apparatus and methods for using the same. More specifically, the present invention relates to methods and apparatus for the extraction of tissue from an enclosed body cavity such as a bone marrow cavity. Specifically, the present invention relates to a method and apparatus for increasing the efficiency of harvesting and processing mesenchymal stem cells and physiological fluids for use in medical treatment applications and medical research.

BACKGROUND OF THE INVENTION

Mesenchymal stem cells, which for purposes of brevity will be referred to herein as ("MSC" or "MSC's"), are stromal or connective tissue cells which are found primarily in umbilical cord blood and bone marrow. Unlike hematopoietic stem cells ("HSC") which contribute to the formation of red blood cells, MSC are capable of differentiating into a variety of cell types such as bone, cartilage, muscle and fat cells. While the cell differentiation phenomenon observed in MSC's is not fully understood, medical research has established that MSC are remarkably capable of contributing to a patient's healing and tissue regeneration processes following injury or surgery.

Allogenic MSC treatments, or treatments with MSC obtained from a different donor, are closely regulated by the FDA and other regulatory agencies as a drug for safety reasons. However, treatments of patients using autologous MSC, or MSC which are self-produced independently of outside materials, offer attractive treatment alternatives. FDA guidelines require that autologous human cells, tissues and cellular and tissue products (HCT/P) be only "minimally manipulated" and used within a short period of time, preferably one hour or so following harvesting from the patient; however, they can be used as long as within 12 hours if circumstances dictate. "Minimally manipulated" means that the processing of the HCT/P does not alter the relevant biological or original characteristics of cells or tissues (21 C.F.R. § 1271 3(f)(2)). Accordingly, devices and techniques that fall within the FDA guidelines for harvesting, isolating and concentrating a patient's MSC in a form that may be reinjected into the donor patient for the treatment of physiological problems are needed.

Conventional methods and devices for harvesting and processing cells and physiological fluid for laboratory and medical study and use include, for example, aspiration of bone marrow from bone for producing stem cell concentrate. Exemplary prior art methods and devices involve multiple aspirations of bone marrow cells (BMC) from the patient's posterior iliac crest. Access to the internal cancellous bone, bone marrow and bone marrow blood residing inside the outer cortical bone layer of the ilium is achieved by creating an aperture in the cortical bone with a sharp instrument such as a trocar. An aspiration needle, for example, a Jamshidi bone marrow biopsy needle, is then inserted through the aperture into the interior trabecular compartments within the crest where the MSC are found in their highest concentrations. However, a significant problem associated with conventional methods for harvesting and processing cells and physiological fluid (including the aspiration of bone marrow from bone for producing stem cell concentrate) is that a less than desirable amount, type or quality of cells or physiological fluid may be harvested and subsequently processed.

Various prior art systems, methods and devices for BMC harvesting have been disclosed which attempt to address the problems described above. For example, U.S. Pat. No. 5,456,287 issued to Stark on Oct. 10, 1995, (the '267 patent), discloses bone marrow harvesting and biopsy systems and methods which involve inserting a hollow, threaded bone screw or pin into a patient's bone and then applying a negative pressure to withdraw the bone marrow through the hollow portion.

Stryker Neuro Spine ENT of Kalamazoo, Mich. markets an ultrasonic aspiration device under the tradename "SONOPET" which delivers ultrasonic energy to targeted soft tissue. The SONOPET aspiration device selectively harvests tissue having high water content, generally believed to include unhealthy tissue such as fatty tissue and tissue having lesions. However, the device and operating process does not address the efficiency problems noted herein regarding MSC and MSC-like cell harvesting.

Provencher discloses a tissue sample needle and method in U. S. Patent Application Publication No. US 200710142744 published on Jun. 21, 2007 (the "'744 publication"). However, Provencher's approach necessitates sampling at different locations to obtain sufficient stem cell quantities.

Kraft et al. disclose a device and method for rapid aspiration and collection of body tissue from within an enclosed body space in U.S. Pat. No. 7,462,181 B1 issued Dec. 9, 2008 (the "181 patent"). The '181 patent discloses the use of an aspiration cannula which is inserted into the body cavity along different paths through the same aperture in the outer cortical bone layer. While ostensibly providing a faster and less painful process by virtue of using only a single aperture formed in the patient's cortical bone structure, the type, quality and/or amount of BMC collected remains unaddressed.

More recently, in U.S. Pat. No. 8,048,678 B2 (the "'678 patent"), Duffy, Jr. et al. disclose a cell separation method and apparatus which isolates a "fraction of interest" from a physiological fluid sample. While the '678 patent discloses an improved processing method and apparatus, it does not address the actual harvesting technique, which is performed using conventional techniques known in the prior art.

Accordingly, a need exists for an improved method and apparatus for the harvesting and processing of cancellous bone, bone marrow and bone marrow blood for producing mesenchymal stem cell concentrate and other physiological fluids which addresses the combination of problems not solved by the prior art.

SUMMARY OF THE INVENTION

The stated problems and other needs in the art as apparent from the foregoing background may be addressed in accordance with the methods and apparatus of the present invention as set forth in various embodiments disclosed herein.

In one embodiment, a method for harvesting a patient's mesenchymal stem cells is provided which includes inserting a Jamshidi-type needle, (also known as a stylet or trocar)

having a preselected diameter or size and a cannula extending circumferentially about and along the length thereof into the cortical bone at a preselected location on a patient's skeletal system forming an aperture therein, removing the stylet, advancing the cannula into the patient's bone marrow to obtain a cancellous bone plug, and aspirating bone marrow material, blood, MSC and MSC-like cells through a cancellous bone plug positioned in the cannula, to increase the harvested MSC cell count.

In another embodiment, a cannula used in conjunction with a Jamshidi-type needle has external or male threads formed on an end thereof, the threaded end of the cannula being adapted to be controllably threaded into and/or withdrawn from an aperture formed in a patient's cortical bone.

In still another embodiment, a larger diameter Jamshidi needle or stylet is movably deployed within an outer cannula having at least one externally-threaded end, the needle being adapted to create an aperture in the patient's cortical bone structure at a preselected location, removing the stylet once the sharp tip penetrates the cortical bone, threading the tip of the cannula into the cortical bone to maintain its position, advancing an inner cannula having multiple apertures located on a body portion thereof into the bone marrow, obtaining a bone plug, and aspirating marrow blood through the bone plug as the cannula is advanced or retracted. The inner cannula may be threaded such that it is advanced or retracted through the outer cannula in a more controlled fashion during aspiration.

In yet another embodiment, a method for harvesting a patient's mesenchymal stem cells is provided which includes creating an aperture in an outer layer of cortical bone at a preselected location on a patient's skeletal system, positioning a guide device over the aperture which is adapted to receive and guide an aspirating device to multiple locations within a cavity or compartment within the patient's skeletal system containing cancellous bone, bone marrow, blood and MSC, obtaining at least one cancellous bone plug from within the cavity for insertion into the aspirating device, aspirating one or more samples of the patient's bone marrow blood and MSC's through the bone plug, thereby increasing the concentration of MSC's in each sample.

In another embodiment, the aspirant contains red blood cells, and the harvesting method further includes the step of lysing the red blood cells.

In still another embodiment, the aspirant contains red blood cells and platelets, and the harvesting method includes lysing the red blood cells and the platelets.

In another embodiment, the bone plug is removed from the aspiration device and inserted onto a filtering apparatus wherein the bone plug is repeatedly flushed with autologous media collected from the patient, thereby further enhancing the concentration of harvested MSC's.

In still another embodiment, a harvested and filtered MSC sample is centrifuged to further separate and concentrate the MSC.

In yet another embodiment, an apparatus for harvesting a patient's mesenchymal stem cells and obtaining at least one cancellous bone plug from the patient is provided.

In an embodiment, a processed aspirated solution having an isolated and maximized concentration of a patient's MSC's is reinjected into the patient at a specific treatment site in the patient.

In another embodiment, a processed aspirated solution having an isolated and maximized concentration of a patient's MSC's is applied to patient's skin to treat dermatological and cosmetic conditions.

In an embodiment, a processed aspirated solution having an isolated and maximized concentration of a patient's MSC's is reinjected intravenously into the patient for therapeutic treatment of the patient.

In yet another embodiment, an apparatus for expanding a patient's mesenchymal stem cells is provided.

In still another embodiment, a patient's mesenchymal stem cells are expanded following flushing the bone plug.

These and other features of the present invention will be apparent from the accompanying description of the invention, drawings, diagrams and supplemental supporting materials provided herein.

BRIEF DESCRIPTION OF THE DRAWINGS

FIG. 1A is a posterior plan view of a portion of a human pelvic structure showing the sacrum and a portion of the right ilium thereof;

FIG. 1B is a side plan view of a trocar adapted for creating an aperture in a preselected portion of a patient's skeletal system in accordance with the present invention;

FIG. 1C is a side perspective view of a trocar positioned on a patient's ilium in accordance with an embodiment of the present invention;

FIG. 34A is a bar graph illustrating the enhanced yields of a distinct MSC subpopulation obtained in accordance with the embodiments of the present invention;

FIG. 34B is a bar graph illustrating the enhanced yields of another distinct MSC population obtained in accordance with the embodiment of the present invention;

FIG. 34C is a bar graph illustrating the enhanced yields of still another distinct MSC population obtained in accordance with the embodiment of the present invention;

DETAILED DESCRIPTION OF THE INVENTION

Figure 2:
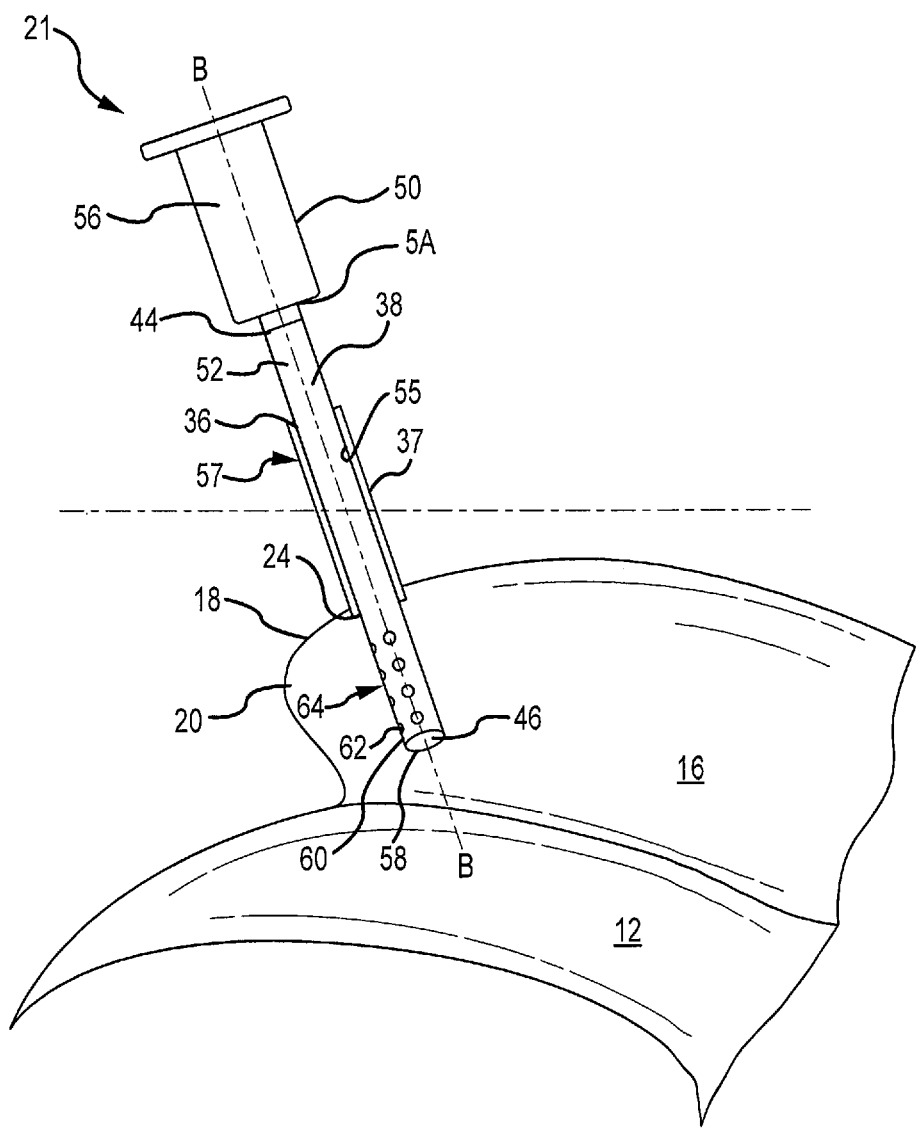
FIG. 2 is a partial sectional view of the patient's ilium as shown in FIG. 1C having an aspiration device positioned in an aperture formed in a posterior portion of a patient's ilium in accordance with an embodiment.

It should be noted that the present description is by way of illustration only, and that the concepts and examples presented herein are not limited to use or application with any single system or methodology. Hence, while the details of the system and methods described herein are for the convenience of illustration and explanation with respect to the exemplary embodiments, the principles disclosed may be applied to other types of mesenchymal stem cell harvesting systems and methods without departing from the scope of the present invention.

Apparatus

Referring now to FIG. 1A, a posterior view of a portion of a patient's skeletal system is shown generally at 10. The portion illustrated includes segments of the patient's pelvis, specifically the sacrum 12 and a partial view of the iliac crest 14 which comprises the upper or top portion of the ilium 16. The ilium, like other bones of the skeletal system, includes a hard outer cortical bone material which forms an outer layer 18 around an internal cavity 20. The internal cavity 20 includes trabecular cavities formed by trabeculae (not shown), a soft, spongy bone material medically known as cancellous bone, bone marrow, blood, nerve structures, vascular components, and a variety of complex cells which perform a host of different regenerative and support functions for the body. In essence, the internal cavity within the cortical bone is the site of specific microenvironments or niches within the enclosed bone marrow for the generation of the cells, proteins, and other cellular-type moieties found within the cancellous bone. By way of example, these cells include hematopoietic stem cells (HSC) which are the source of blood cells, mesenchymal stem cells (MSCs) and MSC-like cells including CXCL12-abundant reticular (CAR)-cells, Leptin-receptor expressing cells among others, all of which play a role in cell generation. MSCs and MSC-like cells have proven useful for therapeutic treatments of injuries, inflammation, pain, cosmetic issues and other medical conditions, and the efficient harvesting thereof is of specific interest in modern medical science.

Referring to FIGS. 1-6, the elements of embodiments of an apparatus 21 for harvesting a patient's mesenchymal stem cells are illustrated in greater detail. As best shown in FIGS. 1A, 1B and 1C, the harvesting apparatus includes an elongate perforating device 22, by way of example, a trocar, which is adapted to form an aperture 24 in a preselected portion of a patient's skeletal system extending through the outer layer 18 of cortical bone into the cavity 20. The perforating device includes a proximal end 26, a distal end 28 and an elongate body portion 30 extending therebetween along a longitudinal axis A-A. A handle, for example, a T-shaped handle 32 is secured to the proximal end 26, and a sharp tip 34 is formed on the distal end 28, the tip being adapted to penetrate through a patient's skin 19 and then through the outer layer 18 formed by the cortical bone. The proximal end of the trocar may also include male threads 35 formed thereon being adapted to engage mating internal female threads formed in a cannula, as will be described below in greater detail.

Referring now to FIG. 2, portions of the harvesting apparatus 21 are shown in greater detail in position at the preselected location on the patient's ilium following the forming of the aperture 24 therein by the perforating device. The apparatus further includes an outer cannula 36 having an elongate tubular body portion 38 including concentric external and internal surfaces 40, 42 (FIG. 3A) extending along a longitudinal axis B-B intermediate proximal and distal open end portions thereof 44, 46. The tubular body of the cannula is removably positioned on the trocar and adapted to be seated on the outer layer of the cortical bone at the location of the aperture. After the aperture is formed, the perforating device or trocar is withdrawn leaving the cannula in position as shown.

Figure 3A:
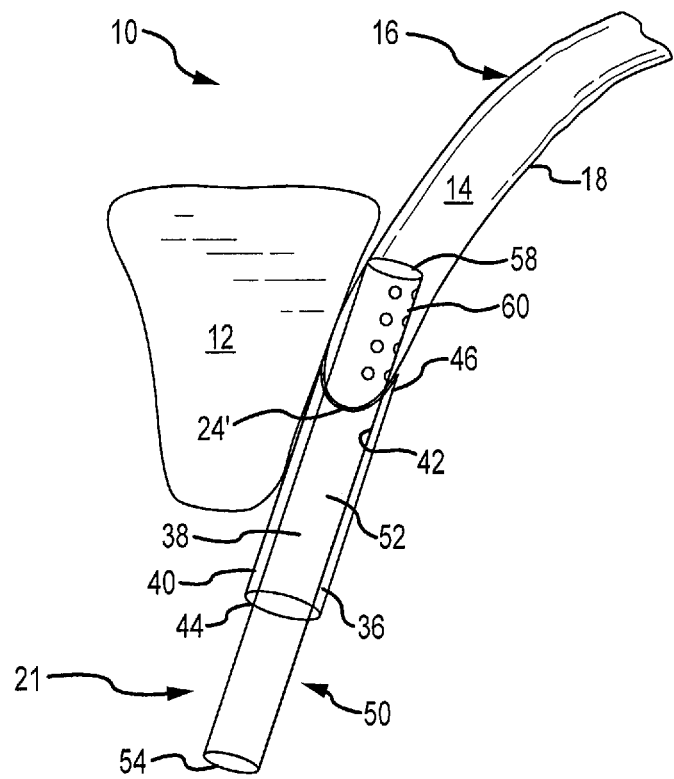
FIG. 3A is a partial sectional view of an aspiration device positioned in an aperture formed in a posterior inferior portion of a patient's ilium in accordance with an embodiment.
Figure 3B:
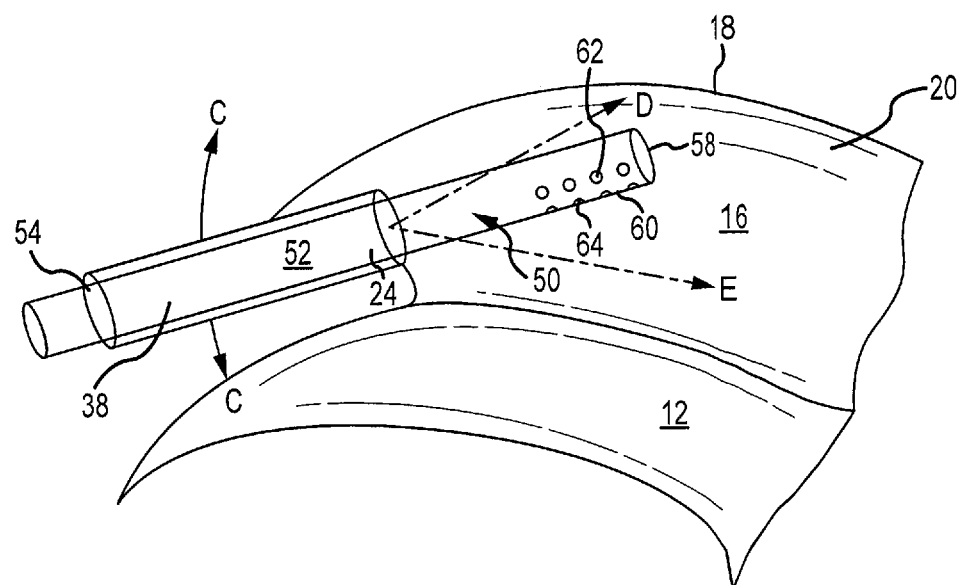
FIG. 3B is a partial sectional view of an aspiration device positionable along different trajectories within a posterior inferior portion of a patient's ilium in accordance with an embodiment.

The cannula is further adapted to receive an aspiration device 50, as depicted in FIGS. 2, 3A and 3B. By way of example and not of limitation the aspiration device may be in the form of a hollow, open-ended biopsy needle having an elongated body portion 52 extending substantially coaxially along axis B-B of the cannula. The body of the aspiration device includes a proximal end 54 having a collection device, by way of example a syringe 56, operatively connected thereto for receiving aspirated material from the internal cavity of the ilium 20. The aspirant is communicated thereto via at least one aperture 58 formed in a distal end 60 of the aspiration device following its insertion into the cavity and in response to suction forces exerted thereon by the collection device.

The body portion of the aspiration device further includes an interior surface 55 and an exterior surface 57. According to particular embodiments, the interior surface 55 of the aspiration device is structured and arranged to have a surface roughness which is substantially rougher than the surface roughness of the exterior surface 57 of the aspiration device. The interior surface so configured is adapted to retain bone graft within the aspiration device received via the aperture 58 upon withdraw of the aspiration device. For example, the exterior surface may comprise a roughness between about 2 micro inch arithmetical average (μinAA) and 63 μinAA (or approximately 0.05 micrometers roughness average (μmRa) and 1.6 μmRa) while the interior surface may comprise a roughness between 250 μinAA and 1000 μinAA (or approximately 6.3 μmRa and 25 μmRa). In various other aspects, the roughness differential between interior and exterior surfaces may vary from about 393% to about 500%, from about 500% to about 5000%, from about 5000% to about 10000%, from about 10000% to about 50000%, and from about 50000% to about 126,000%. In various additional aspects, the roughness differential between interior and exterior surfaces may be about 393%, about 500%, about 5000%, about 10000%, about 50000% and about 126000%. In various other aspects, the roughness differential between interior and exterior surfaces may range from about 187 μinAA to about 250 μinAA, from about 250 μinAA to about 450 μinAA, from about 450 μinAA to about 650 μinAA, from about 650 μinAA to about 850 μinAA, and from about 850 μinAA to about 1000 μinAA. In various additional aspects, the roughness differential between interior and exterior surfaces may be 187 μinAA, 200 μinAA, 250 μinAA, 300 μinAA, 350 μinAA, 400 μinAA, 450 μinAA, 500 μinAA, 550 μinAA, 600 μinAA, 650 μinAA, 700 μinAA, 750 μinAA, 800 μinAA, 850 μinAA, 900 μinAA, 1000 μinAA, 2000 μinAA, 3000 μinAA, 4000 μinAA, 5000 μinAA, 6000 μinAA, 7000 μinAA, 8000 μinAA, 9000 μinAA and 10000 μinAA. The rough surface may be manufactured via numerous methods know in the art. According to particular embodiments, chemical etching of the interior surface may be performed while avoiding exposure to the exterior surface by the etchant (or if exposed, processed further to reduce surface roughness by e.g., selective electropolishing, grinding, buffing, polishing, etc.). According to particular embodiments, material (e.g., metal) thermal (e.g., plasma) spraying of the interior surface may be performed while avoiding exposure to the exterior surface by the spray (or if exposed, processed further to reduce surface roughness by e.g., selective electropolishing, grinding, buffing, polishing, etc.).

Referring to FIGS. 2 and 3, the distal end 60 of the aspiration device is shown in greater detail. As described above, the distal end may include a single aperture 58 formed at the very tip thereof, or at least one configuration of apertures 62 extending circumferentially about the body portion at a preselected longitudinal distance from the end, or one or more additional configurations of circumferentially positioned apertures 64, each located at a preselected longitudinal distance from the end. In an embodiment, the distal end may also be closed, thus providing the aspiration device the capability of harvesting bone marrow aspirant containing MSC at various levels within the internal cavity.

As shown in FIG. 3A, the apparatus and technique disclosed hereinabove with respect to FIGS. 1 and 2 may be applied to penetrate a patient's skin and the cortical bone of the ilium at a posterior inferior starting point or location 24'. Location 24' is an area of the ilium having less prominence than the location on the crest illustrated in FIGS. 1 and 2. It may be selected to minimize a patient's post-procedure pain level resulting from external contact with and irritation of the aspiration site.

FIG. 3B illustrates features of the novel methodology of the present invention wherein the aspiration device 50 may be redirected to different locations within the cavity 20 to obtain new bone plugs and marrow aspirate without having to extract and reinsert the aspiration device. For example, by pivoting the apparatus in the direction of the arc shown by arrows C-C about the aperture 24 formed in the ilium, bone plug and aspirate material may be harvested along different trajectories and from different areas of the cavity, shown for example, along arrows D and E and the areas in between. The quantity and MSC concentration in the aspirate may be enhanced further by gradual extraction and reinsertion of the apparatus at the same time it is being pivoted, thus creating what may be described as a stirring motion within the cavity 20.

Figure 4:
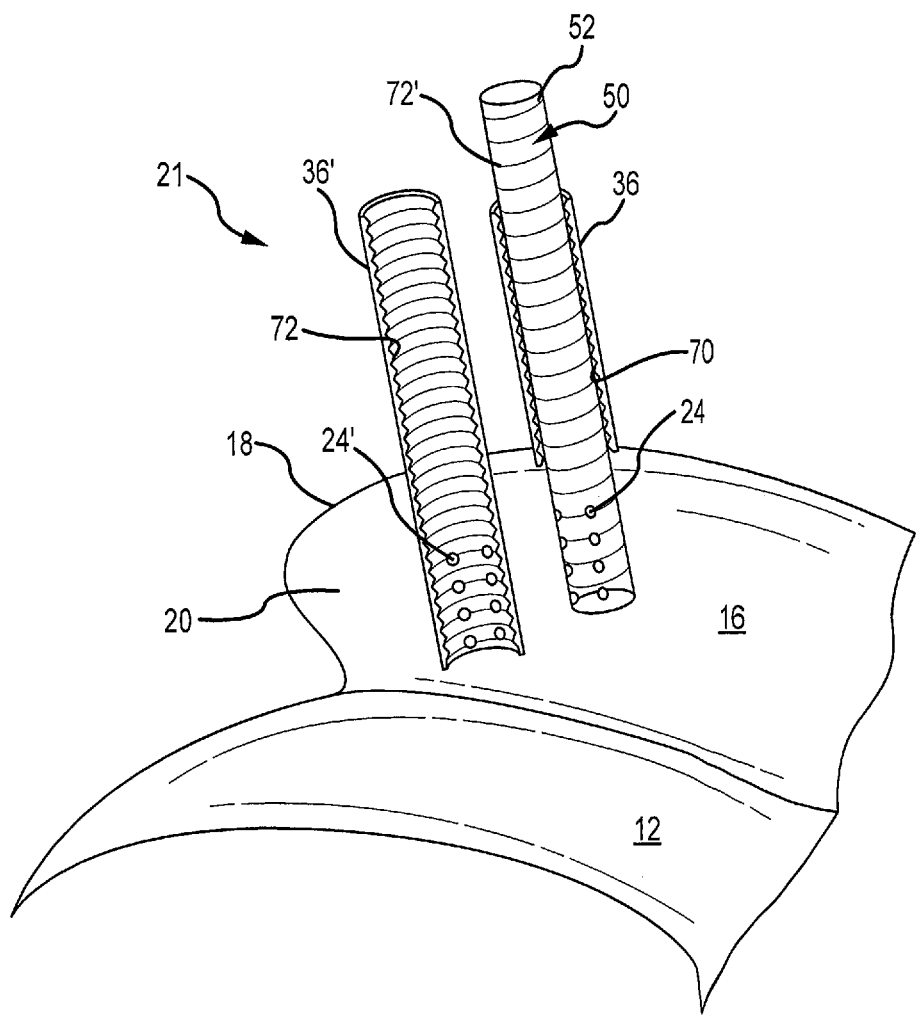
FIG. 4 is a side partial sectional perspective view of a pair of threaded cannulae and an aspiration device positioned in a patient's ilium with a portion of a cannula removed to more clearly illustrate the details thereof in accordance with an embodiment of the present invention.

Referring now to FIG. 4, in accordance with another embodiment of the present invention, a pair of cannulae 36/36' are shown, each having male threads 70 formed thereon and adapted to threadably engage a respective aperture 24/24' formed in the cortical bone, thus permitting the cannula to be controllably retracted during aspiration of the bone marrow aspirant and MSC's from the internal cavity 20 in the ilium. The threads may be formed as a continuous thread or discontinuous thread. Furthermore the threads may be single or dual lead, have a self-tapping distal end portion and/or be configured as a tap pattern. Additionally, the cannula may include female threads 72 formed on the internal surface of the tubular body portion thereof extending between the distal and proximal ends such as shown in the sectional view of cannula 36'. The female threads on the internal surface of the cannula are structured and arranged to threadably engage and cooperate with male threads 72' formed on the elongate body 52 of the aspiration device 50 to provide controlled retraction of the aspiration device during the aspiration process. The threads formed on the elongate body of the aspiration device may be formed as a continuous thread or discontinuous thread. Furthermore the thread may be single or dual lead, have a self-tapping distal end portion and/or be configured as a tap pattern. Additionally, the thread pitch may be constant or variable.

Figure 5A:
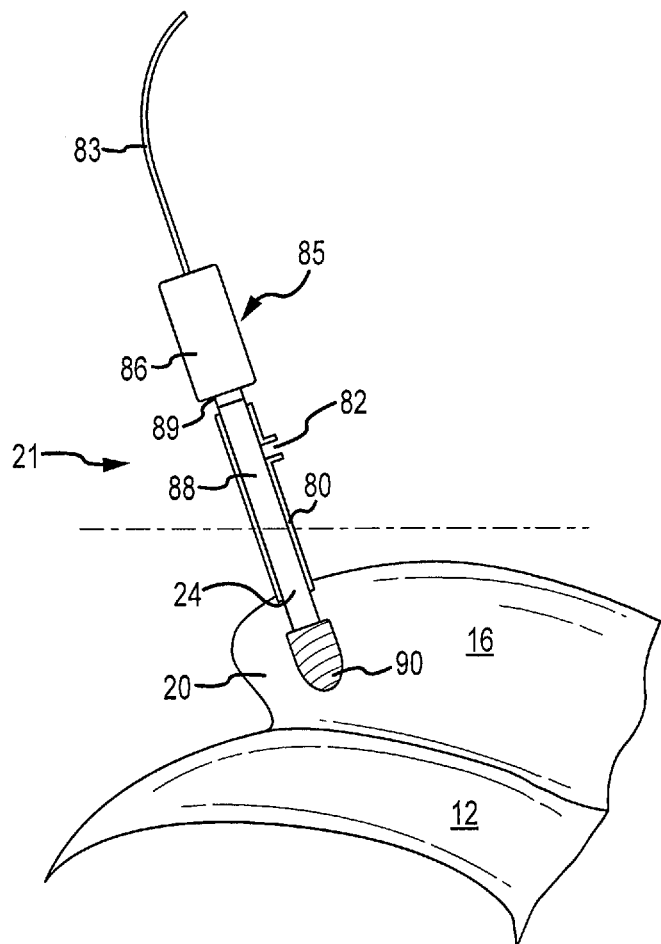
FIG. 5A is a partial sectional side view of an aspiration device adapted to morcellize cancellous bone within the patient's ilium in accordance with an embodiment.
Figure 5B:
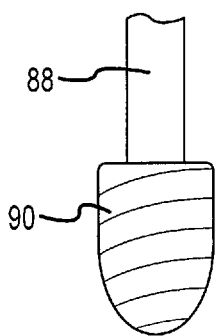
FIG. 5B is an enlarged side plan view of a portion of the aspiration device shown in FIG. 5A.

FIGS. 5A and 5B illustrate yet another embodiment of the present invention in which the aspiration device is adapted to mechanically stir and/or morcellate the cancellous bone material within the internal cavity 20 prior to aspiration thereof. In this embodiment, a cannula 80 is provided which includes a suction port 82 formed therein structured and arranged to draw off aspirant in response to an applied suction force. An agitation or stirring apparatus shown generally at 85 may include a motorized power unit (or a hand powered mechanism) 86 operatively connected to a rod or shaft 88 extending from the power unit through the cannula and into the internal cavity. The power unit is mounted to a proximal end 89 of the cannula, and connected to a source of electrical power via a power cord 83 and cooperates with the suction force in directing aspirant to the suction port 82. A stirring member 90, which by way of example and not of limitation may be a whisk or a brush similar to a femoral canal brush, is secured to an end of the shaft. The stirring member agitates, stirs and morcellates the contents of the internal cavity in response to rotational movement thereof by the motor 86, thereby enhancing the efficiency of MSC harvesting. The stirring member may be configured as a brush with bristles arranged in a helix such that they collectively form an auger or screw conveyer. Furthermore, shaft 88 may be configured as a screw conveyer. According to an embodiment, the bristles may be geometrically configured and formed of a suitable material such as a stiff plastic brush, such that the stirring member permits apposition to the marrow-cortical interface within a region having high concentrations of MSC's without penetrating beyond the outer cortex of the cortical bone and damaging soft tissue.

Figure 6A:
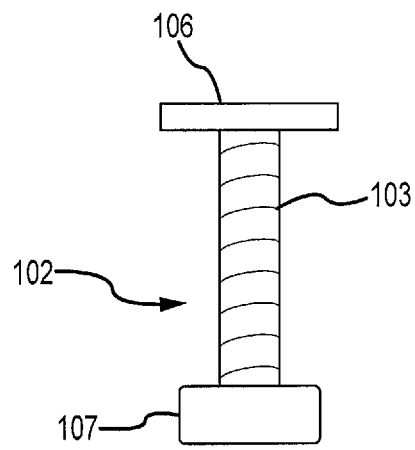
FIG. 6A is a side plan view of a threaded plunger and handle portion of an aspiration device in accordance with an embodiment.
Figure 6B:
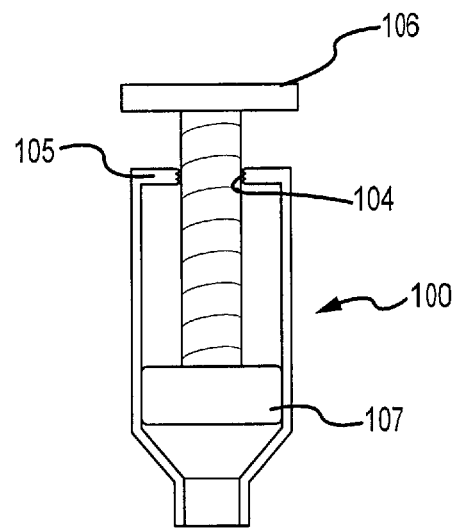
FIG. 6B is a partial sectional side view of a threaded syringe having a threaded plunger as shown in FIG. 6A threadably received therein.

The efficiency and smoothness of the aspiration and MSC harvesting process may be further enhanced by providing a syringe 100 which includes a threaded plunger 102 having threads 103 formed thereon which operatively engage with threads or one or more grooves 104 formed in syringe cap 105 as best shown in FIGS. 6A and 6B. The plunger 102 has a handle 106 secured thereto to facilitate manipulation of the plunger to create a more uniform negative pressure within the syringe via a syringe or piston plug 107 reciprocally positioned within the syringe than would be otherwise obtainable by pulling the plunger manually.

Figure 9:
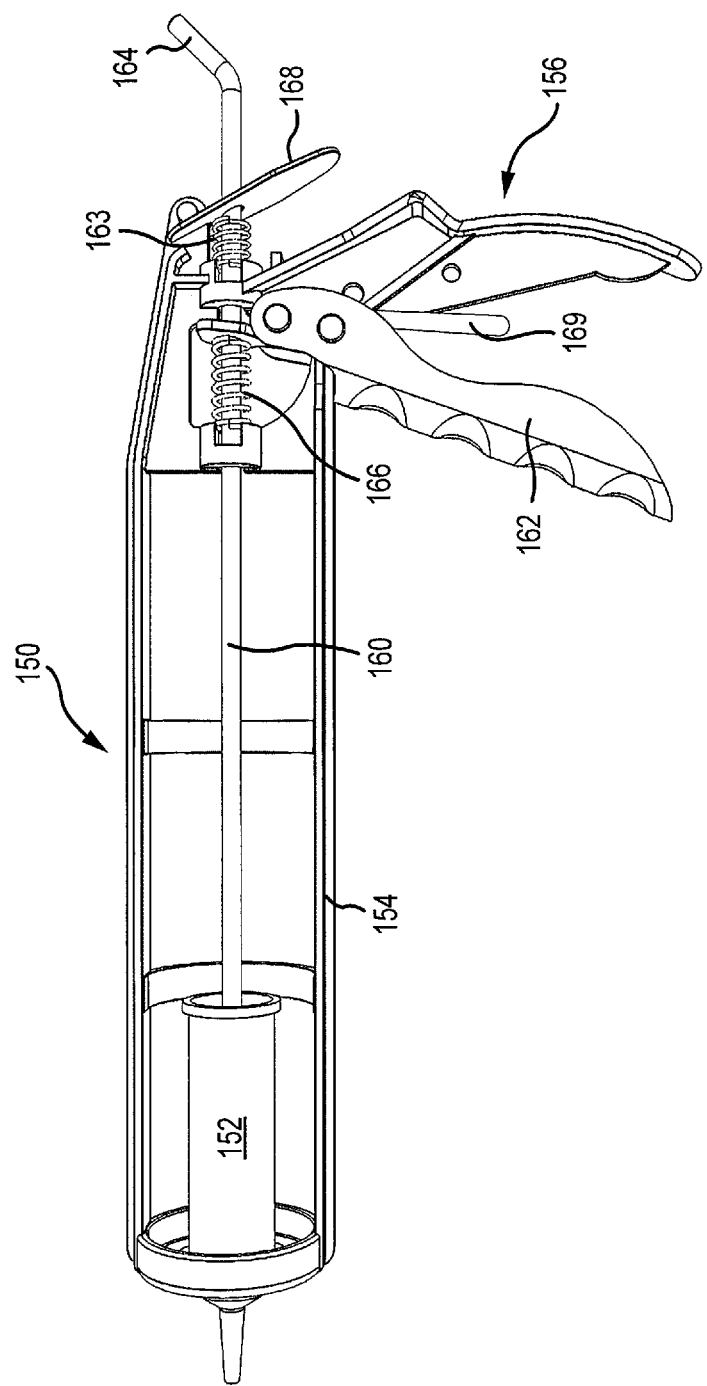
FIG. 9 is a partial side sectional perspective view of a gun-type aspiration device in accordance with an embodiment.
Figure 10:
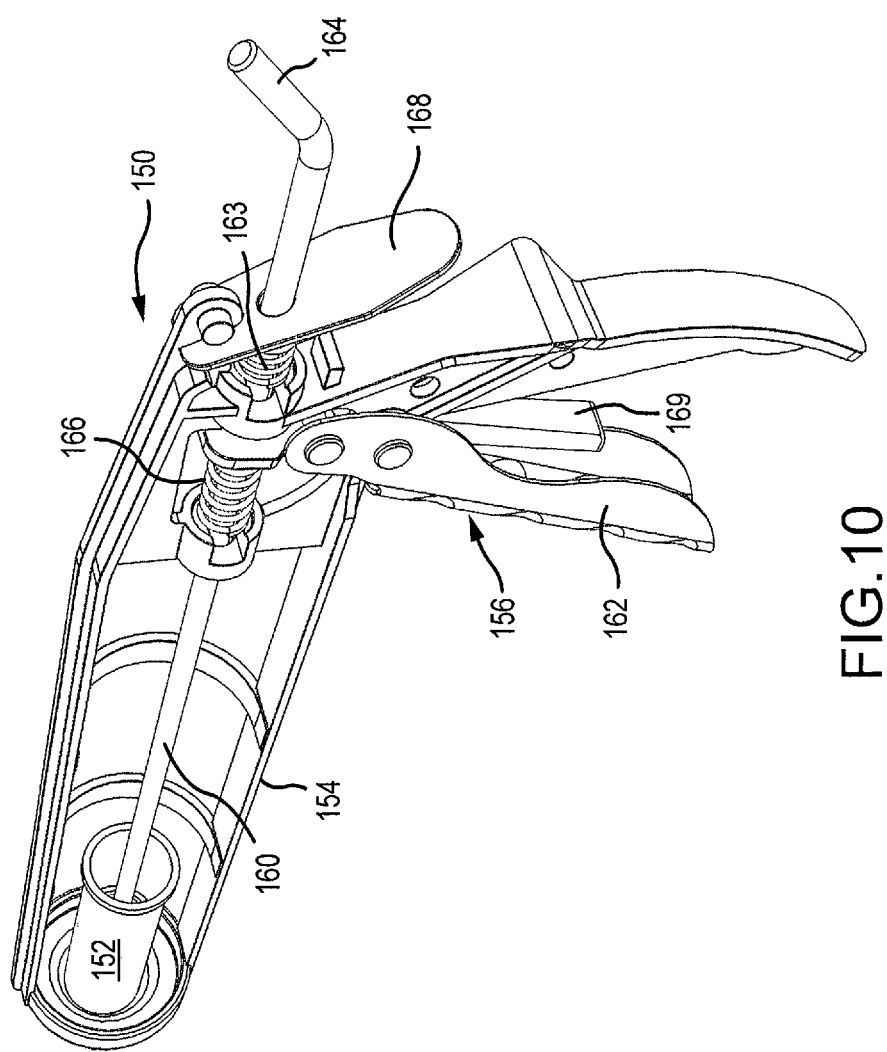
FIG. 10 is a partial side sectional perspective view of the aspiration device of FIG. 9.
Figure 11:
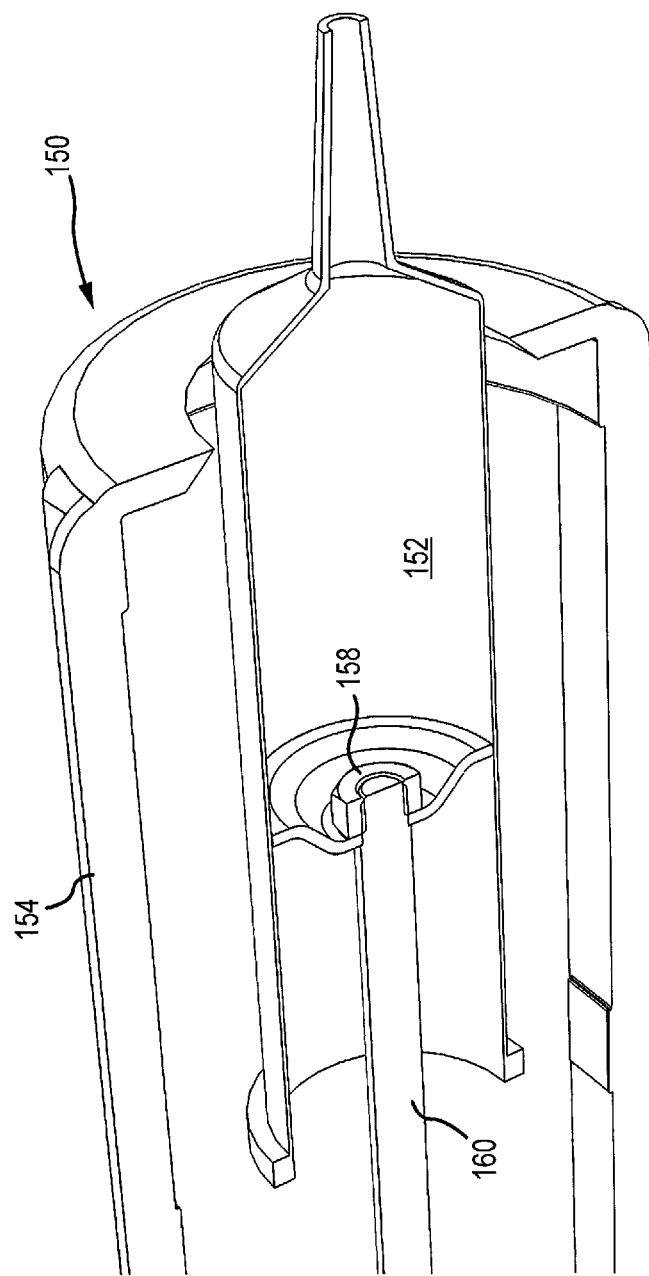
FIG. 11 is an enlarged side sectional perspective view of a portion of the aspiration device of FIG. 9.

Alternatively, the harvesting device may be configured in a manner which is similar to a caulk gun apparatus 150 as shown in FIGS. 9, 10 and 11. In this embodiment, syringe 152 is securely mounted in housing 154 and operatively connected to a control mechanism shown generally at 156. A plunger or piston 158 (FIG. 11) reciprocally positioned within the syringe by rod 160 operatively connected to handles 162 and 164 respectively is biased by spring 166 to controllably and evenly inject autologous media or other suitable fluids into the cortical bone cavity in response to activation of the handle 162. The aspiration of samples of the patients bone marrow blood and MSC's is achieved by depressing locking arm 168 and controllably pulling handle 164 in a direction away from housing 154, thus drawing the aspirant evenly and smoothly into the syringe 152.

According to particular embodiments, the caulk gun apparatus 150 may include a switch 169 to permit the user to select between an aspiration operational mode or a delivery operational mode. When in the delivery mode upon squeezing handle 162 proximally the piston displaces distally thereby delivering or injecting material out of the distal opening of the syringe and, e.g., into a treatment site on or in a patient or into a flushing or filtering apparatus. When in the aspiration mode, upon squeezing handle 162 proximally, the direction of piston movement is reversed, and the piston displaces proximally thereby aspirating material, e.g., from a preselected harvesting site on or in a patient or from a flushing or filtering apparatus into the syringe via the distal opening of the syringe. The switch may select between two transmission mechanisms, for example, springs 163 and 166, which are configured and arranged relative to the handle 162 and rod 160 such that in the aspiration mode, the rod 160 is displaced proximally by the squeezing of the handle 162 via spring 163 and while in the delivery mode, the rod 160 is displaced distally by the squeezing of the handle 162 via spring 166.

Figure 12:
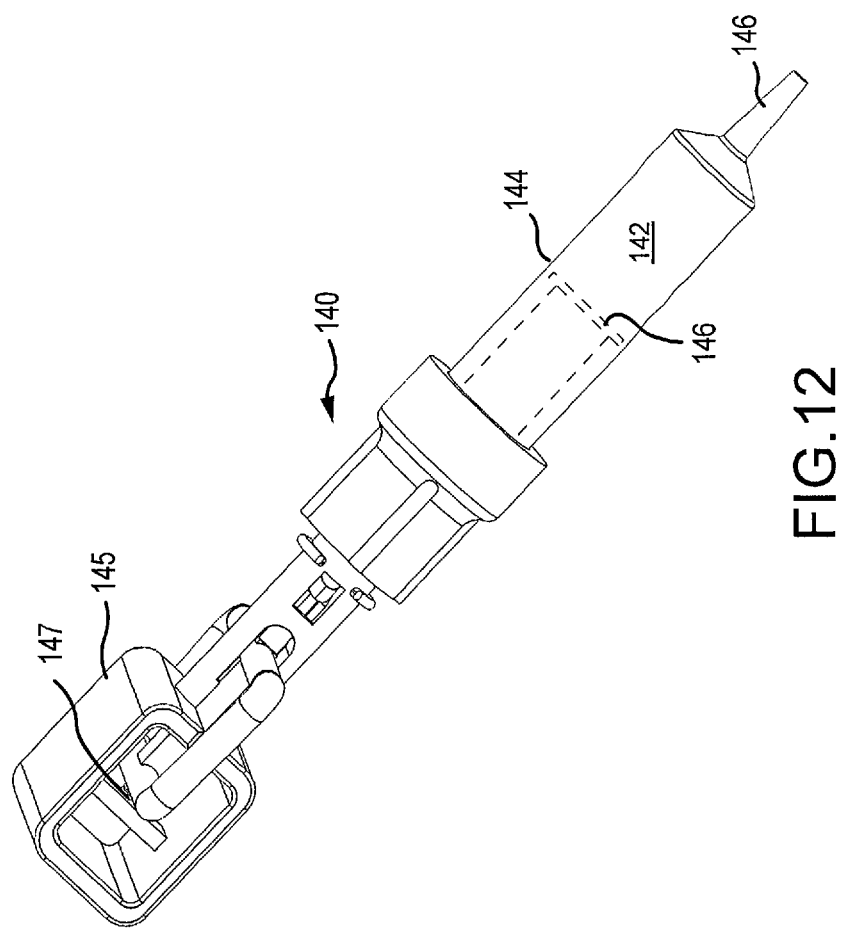
FIG. 12 is a side perspective view of a gun-type aspiration device in accordance with another embodiment.
Figure 13:
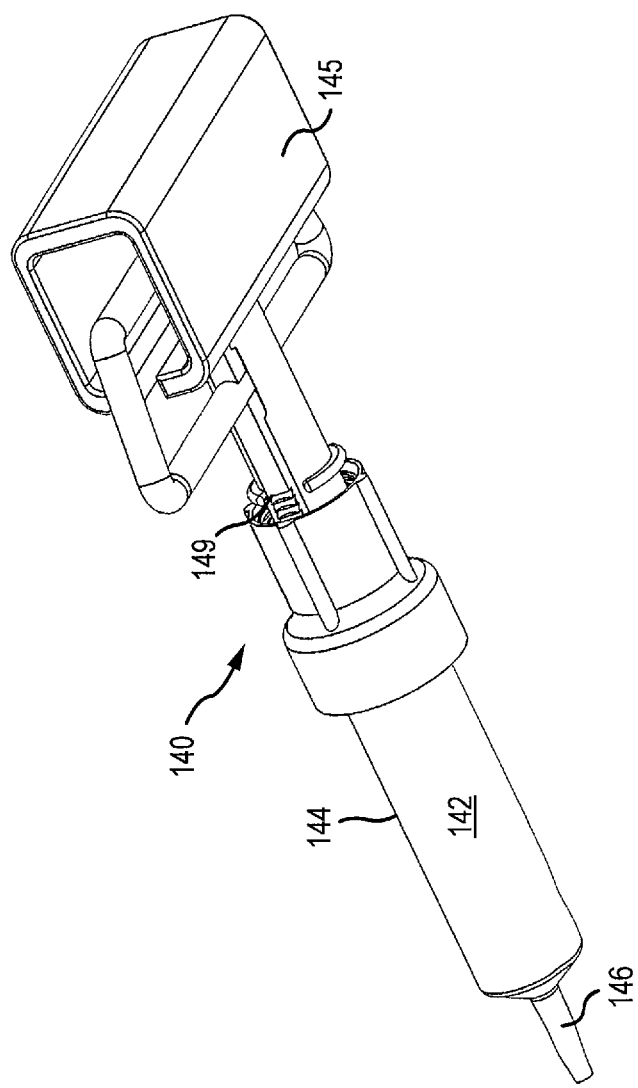
FIG. 13 is a bottom perspective view of the aspiration device of FIG. 12.

FIGS. 12 and 13 illustrate yet another embodiment of an aspiration device 140. Similar in operation to the apparatus 150 of FIGS. 9-11, aspiration device 140 includes a syringe 142 having a hollow cylindrical body member 144 and a tapered end or tip 146 adapted to be inserted into an aperture formed in a cortical bone portion of a patient's skeletal structure as described above or adapted to be received by a fitting (e.g., luer lock or luer slip coupling) at an end of tubing, filter housing, container, conduit or other apparatus capable of storing or providing passage to a fluid. Selective and evenly controlled injection of autologous media or other suitable fluids into the cortical bone cavity, or at a patient treatment site, and withdrawal of a patient's autologous aspirant including bone marrow blood and MSC's is achieved by activation of handle or control mechanism 145 which either advances or withdraws a piston 146 reciprocally positioned inside the body member 144 of the syringe. By way of example and not of limitation, the piston may be controllably advanced or withdrawn to extract aspirate from the patient via activation of the handle mechanism 145 which cooperates with an internal biasing spring 147 and stepped ratchet teeth 149 to permit the practitioner to aspirate efficiently fluid containing high MSC concentrations.

Figure 7:
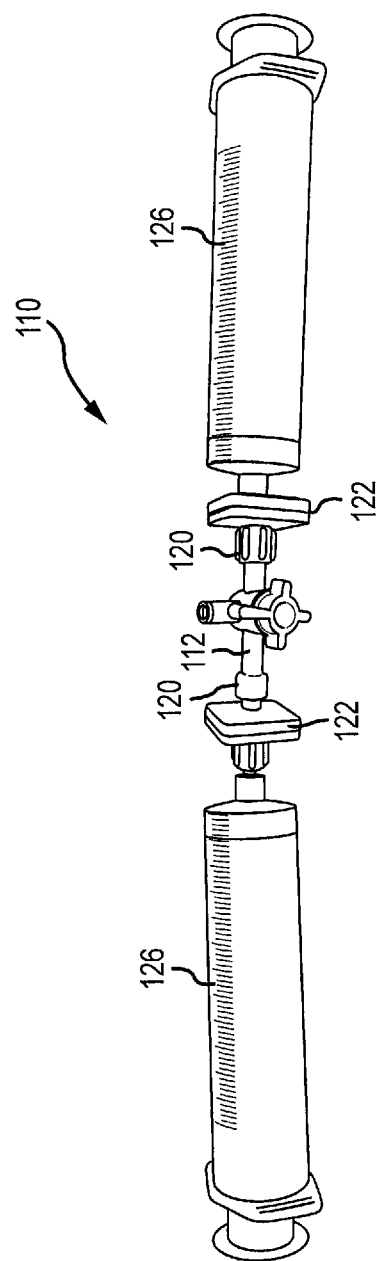
FIG. 7 is a top perspective view of a filtering and washing apparatus in accordance with an embodiment.
Figure 8:
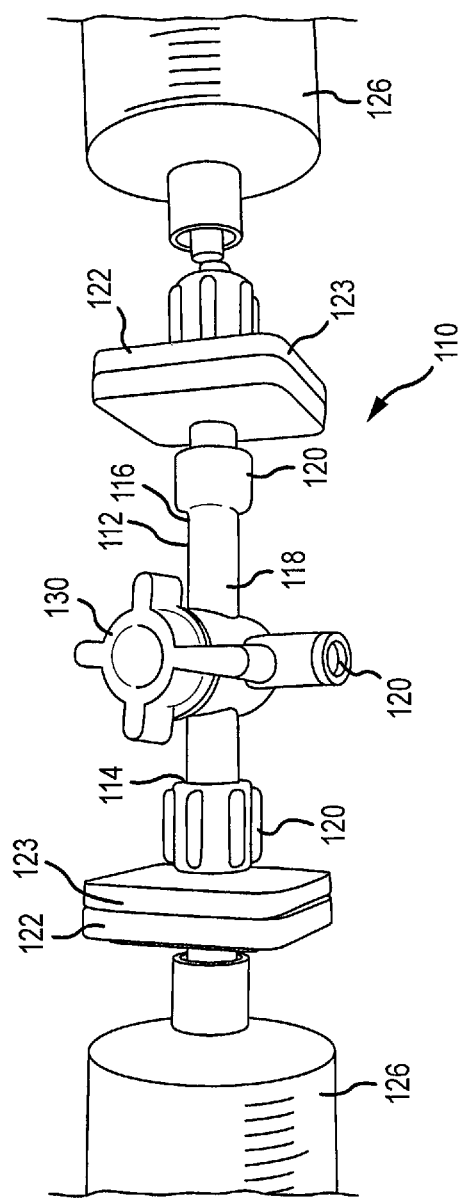
FIG. 8 is an enlarged top perspective view of portions of the filtering and washing apparatus shown in FIG. 7.

Referring now to FIGS. 7 and 8, the elements of a flushing apparatus 110 are shown. The flushing apparatus is structured and arranged to wash, and according to particular embodiments, to filter bone marrow aspirant following its extraction from the interior cavity of a patient's skeletal structure, primarily from the ilium as described above. The flushing apparatus includes a hollow tubular body 112 having first and second ends 114, 116, the body being structured and arranged to receive a cancellous bone plug 118 drawn from a patient's ilium or other bone in his or her skeletal structure. Each end has an adaptor or a cap 120 secured thereto, each cap being operatively connected to and in fluid communication with a flushing chamber 122 which may further contain a suitably sized filter 123. Each flushing chamber, in turn is operatively connected via an adaptor or cap 124 to oppositely disposed bone aspirate receiving apparatus, for example syringe bodies 126 structured and arranged to direct bone aspirate, autologous rinse media drawn from the patient and/or other suitable rinse media back and forth through the bone plug to obtain enhanced or enriched concentrations of MSC (and other desirable cells and fluid) for reinjection into the patient. It is to be understood, however, that the flushing chambers 122 may be omitted from the apparatus of the present invention without departing from the scope hereof. The MSC enriched fluid is drawn off from the flushing apparatus via port 128, which may be selectively opened or closed by a valve 130.

Figure 14A:
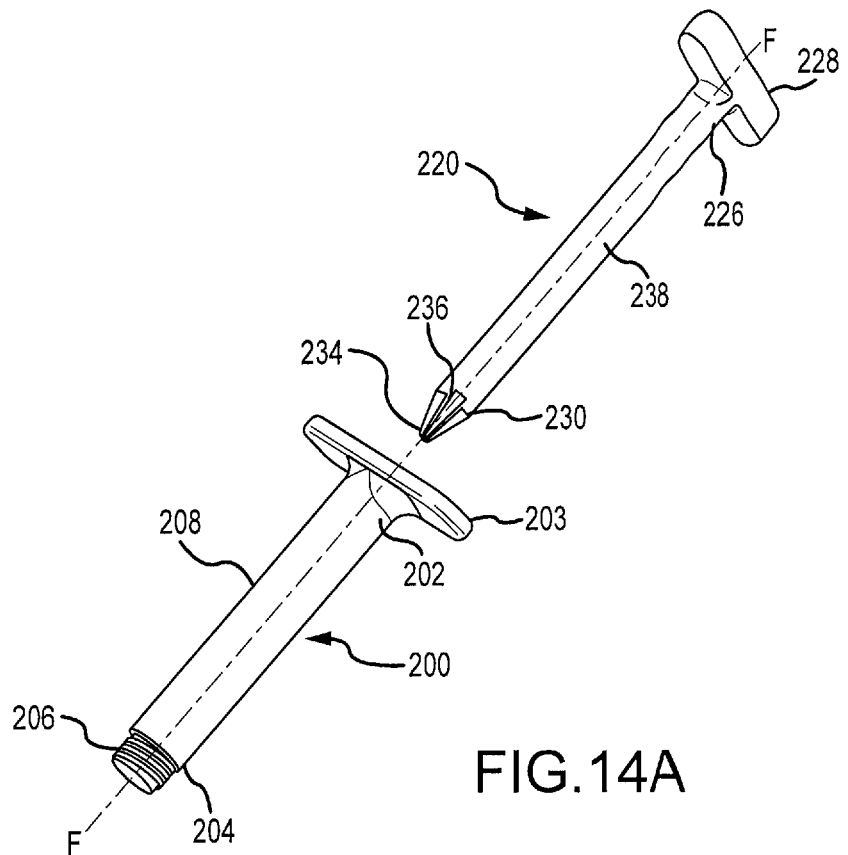
FIG. 14A is an exploded side perspective view of a trocar assembly including an outer cannula having a threaded end adapted to be threadably inserted into the outer cortical bone structure of a patient's skeletal system in accordance with an embodiment.
Figure 14B:
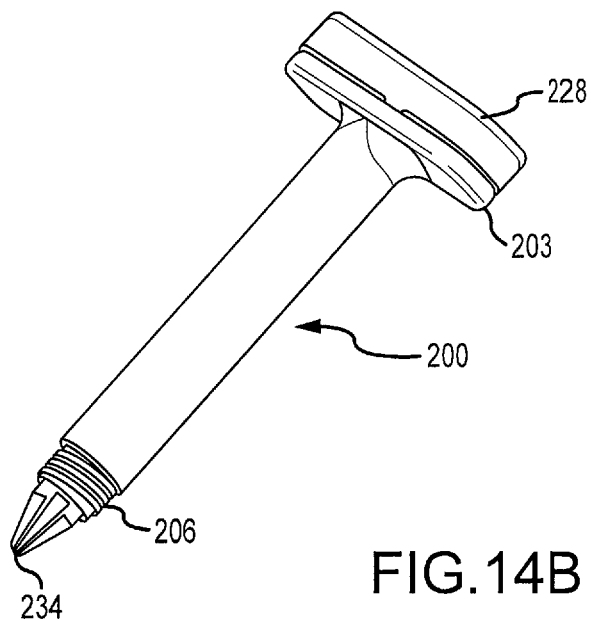
FIG. 14B is a side perspective view of the trocar assembly of FIG. 14A showing the trocar inserted into the cannula.
Figure 15:
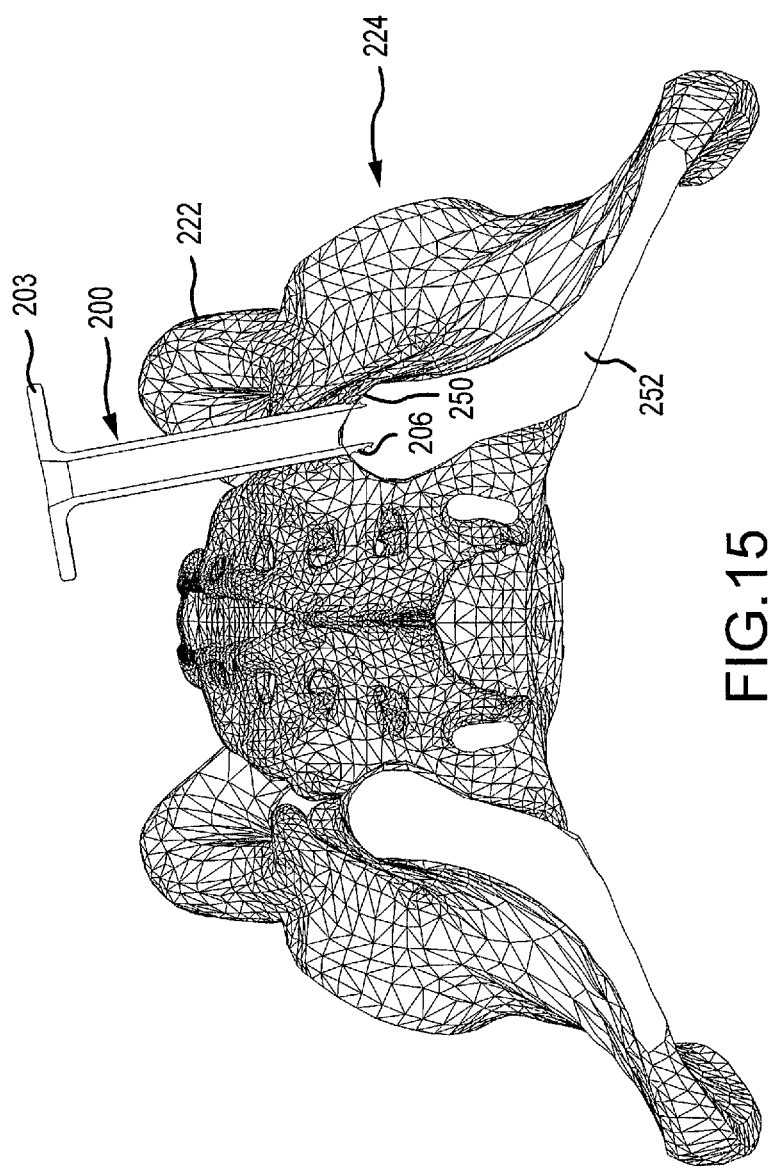
FIG. 15 is a partial sectional top perspective view of a patient's pelvis illustrating a cannula threadably inserted into an aperture formed in the pelvis in accordance with an embodiment.

Referring now to FIG. 14A, a threaded outer working cannula 200 is depicted having a proximal end 202 operatively connected to a handle 203, a distal end 204 having external threads 206 formed thereon, and an elongate cylindrical body portion 208 extending between the ends along a longitudinal axis F-F. A trocar 220 is provided for forming an aperture 250 in the cortical outer bone layer 222 of a portion of a patient's bony anatomy, by way of example the ilium 223 of a pelvis 224 (FIG. 15). The trocar includes a proximal end 226, a handle 228 affixed to the proximal end, a distal end 230 having a sharp pointed tip 234 and sharp tapered cutting edges 236 formed therein. A generally cylindrically shaped rod or body member 238 extends intermediate the proximal and distal ends of the trocar which is adapted to be nested in the cannula 200 generally coaxially along axis F-F, as shown in FIGS. 14A and 14B. The trocar 220 prepares entry into the cancellous bone by morcellizing the cortical bone 222 forming the aperture 250 extending therethrough into a cancellous bone cavity 252. Then the outer cannula 200 is rotated to thread it securely into position with respect to the cortical bone.

Figure 16:
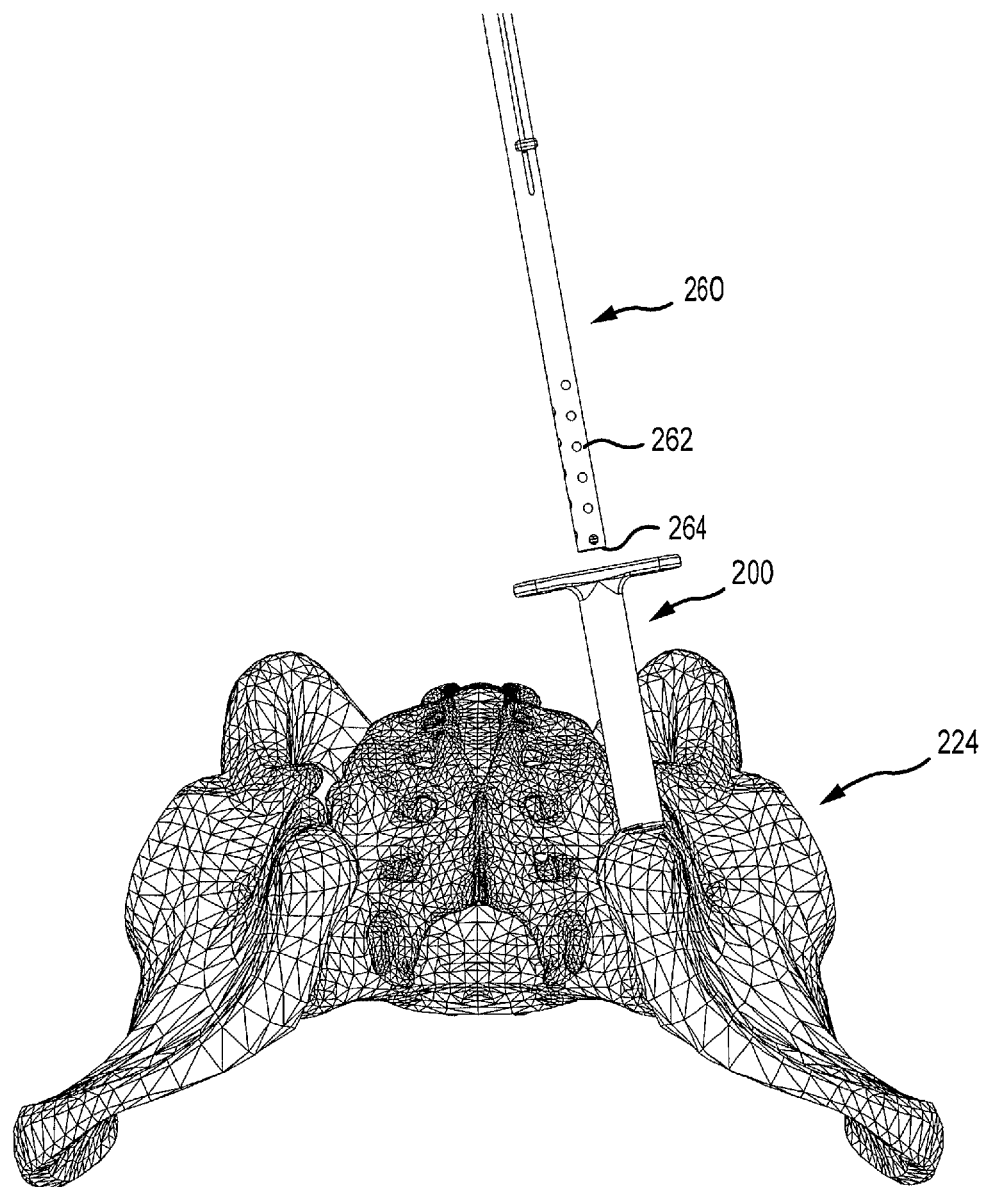
FIG. 16 is a side perspective view of a patient's pelvis shown in FIG. 15 depicting an aspiration device positioned for insertion into the cannula.
Figure 17:
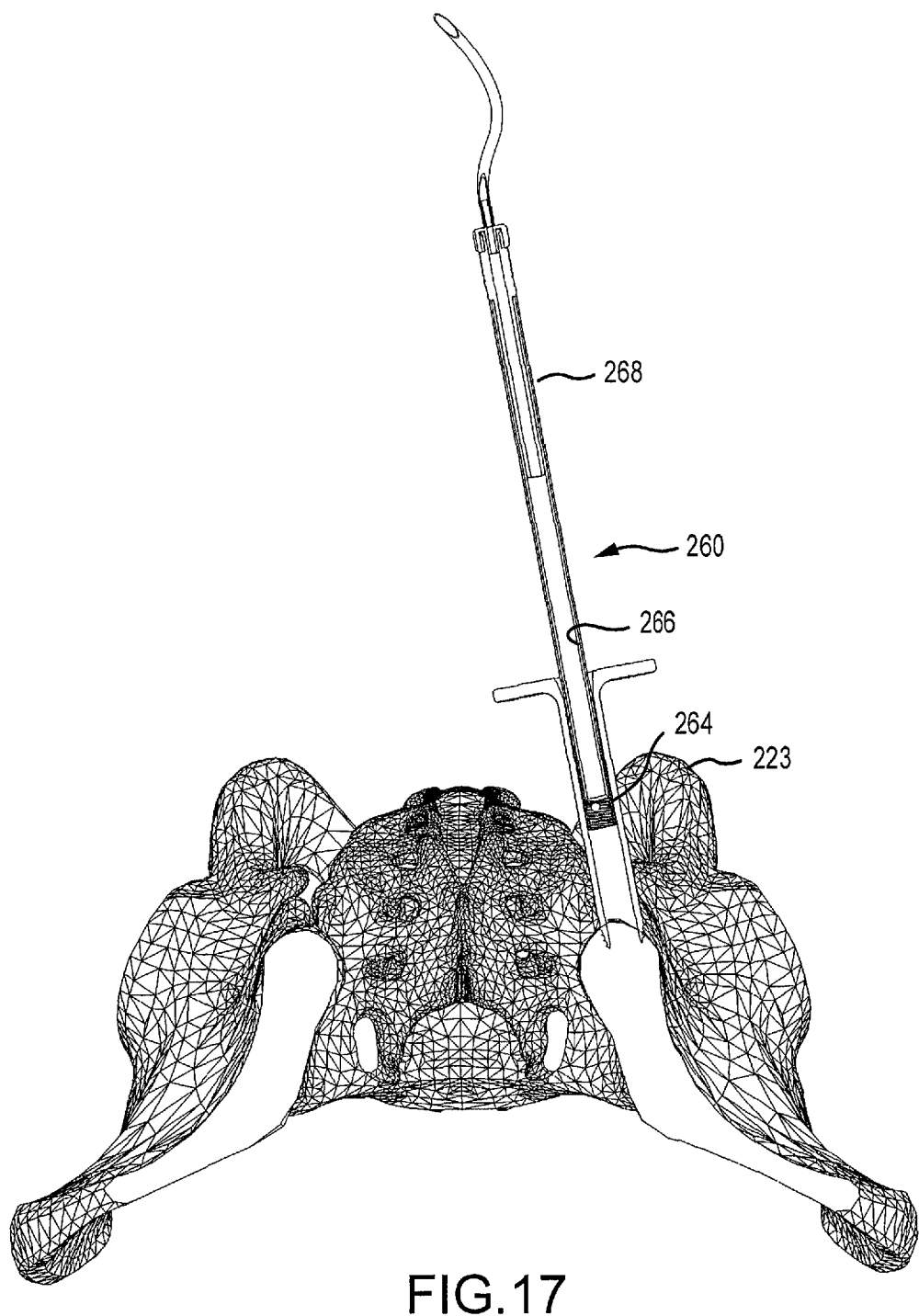
FIG. 17 is a partial sectional side perspective view of a patient's pelvis shown in FIGS. 15 and 16 illustrating an aspiration device partially inserted in the cannula.

Referring to FIG. 16, the trocar is then removed and a tube 260 having a plurality of perforations or apertures 262 formed therein at selected locations and internal buttress threads 264 formed in an inner cylindrical surface 266 thereof (FIG. 17) is advanced through the outer working cannula up to the bone, whereupon it is rotatably advanced (or simply linearly advanced without rotational forces) fully into the cancellous bone. A hollow tube 268 is located within the perforated tube to selectively occlude certain perforations in the tube when employing suction via a syringe or other aspiration device such as discussed above with respect to the embodiments of FIGS. 9-13 to obtain one or more cancellous bone plugs and aspirate material from within the patient's ilium cavity. Once sufficient aspirate has been obtained, the perforated tube containing cancellous bone plug material is removed while leaving the outer working cannula in place. The bone plug is then removed for further processing in a flushing apparatus as detailed above with respect to the apparatus of FIGS. 7 and 8. The outer working cannula 200 is repositioned within generally the same cortical entry point such that a second trajectory is provided for another round of aspiration following the same steps above (less the trocar steps). According to particular embodiments, the above steps may be performed via a third, fourth or further trajectories via repositioning.

Figure 18:
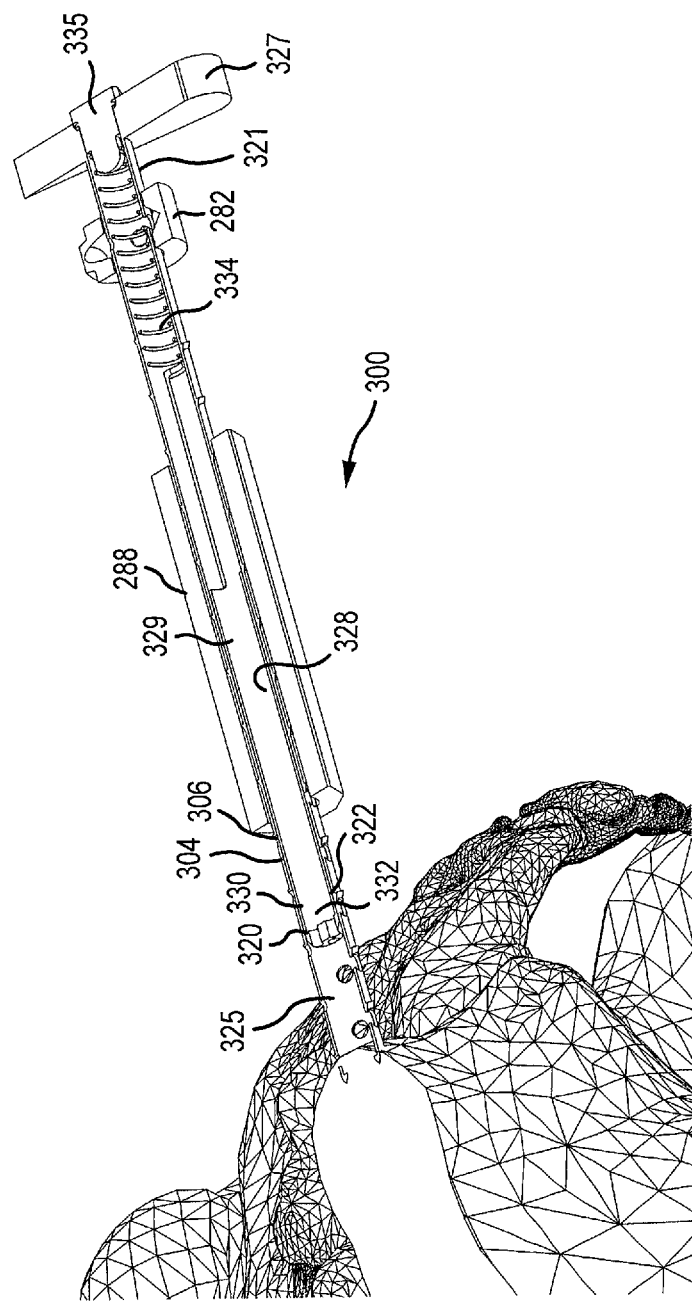
FIG. 18 is a side sectional perspective view of the components of an MSC harvesting system inserted in a patient's pelvis in accordance with an embodiment.

Referring to FIG. 18, a harvesting system 300 is illustrated which includes a perforated tube 304 having a plurality of apertures or perforations 306 formed therein, a proximal end 321 having a T-handle 327 secured thereto, and a circumferential choke 320 at a distal end 322. The distal end is configured to receive cancellous bone such that within a region 325 defined by the choke, the cancellous bone is in a compressed condition to partially occlude the tube distal end, thereby permitting higher than otherwise flow via the perforations. The perforations are selectively opened or closed via a "float" 328. The float includes a cylindrically shaped body 329 having a distal end 330 further having at least one opening 332 formed therein and configured to about the compressed cancellous bone located within the perforated tube. The float may be distally biased via a spring 334 supported by a plug 335, the plug being threadably engaged with the proximal end 321 of the perforated tube such that the plug occludes the proximal end of the tube.

Figure 19:
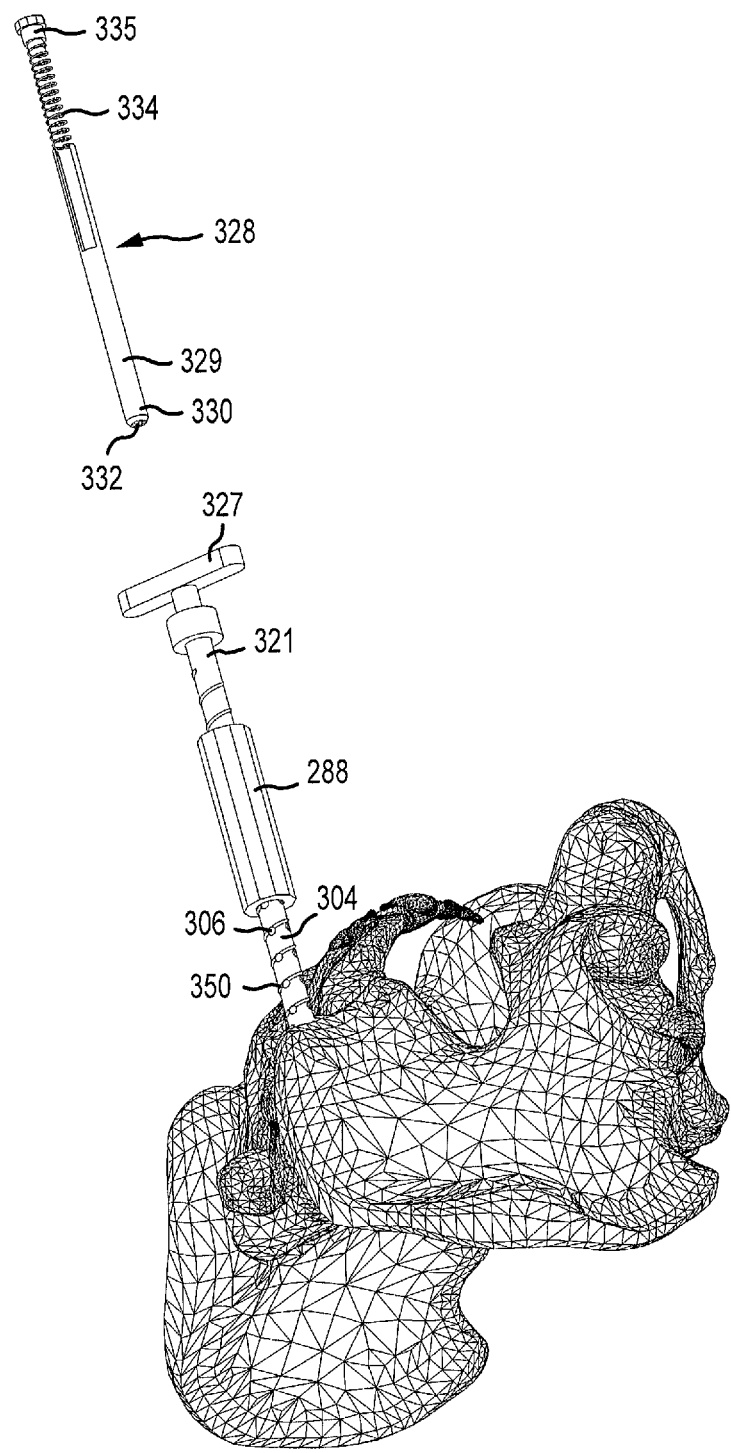
FIG. 19 is an exploded side perspective view of the MSC harvesting system of FIG. 18.
Figure 20:
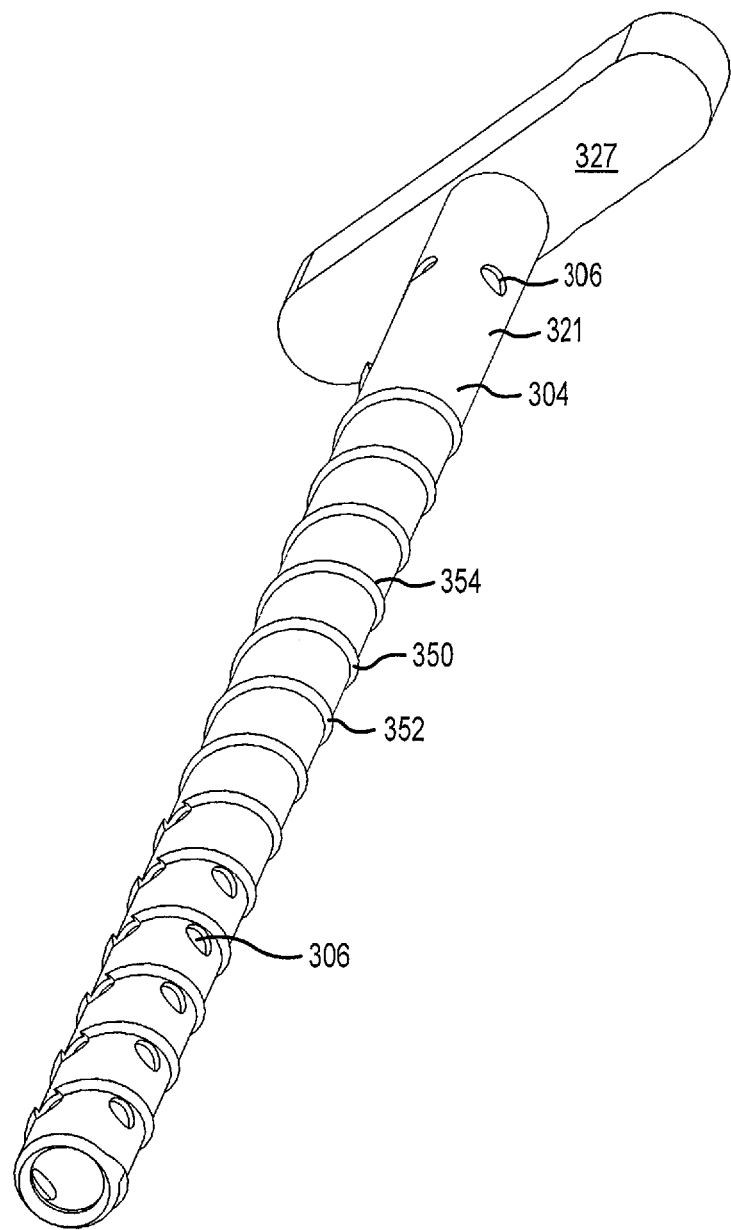
FIG. 20 is a bottom perspective view of a perforated tube member of the MSC harvesting system of FIGS. 18 and 19.
Figure 21:
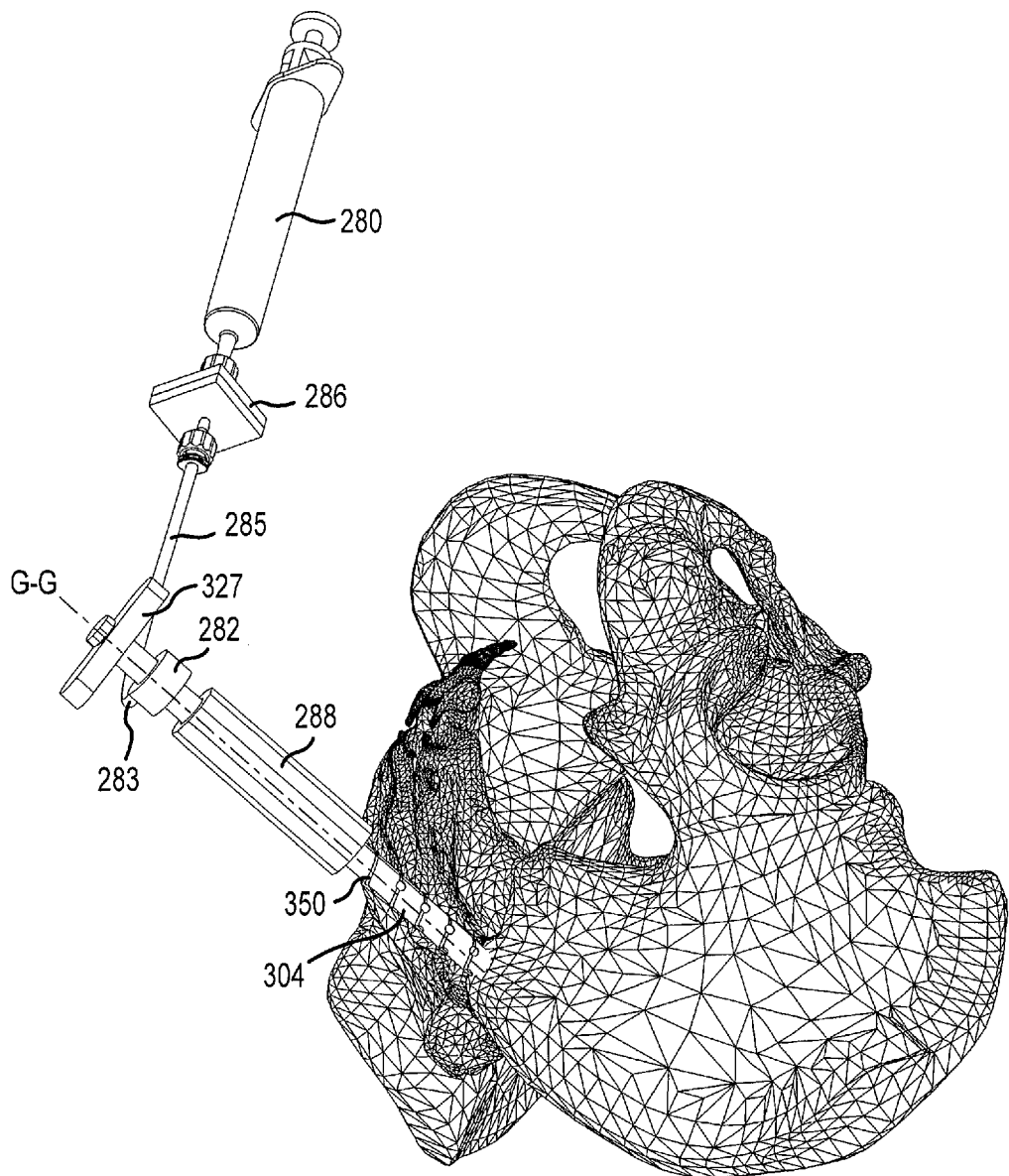
FIG. 21 is a bottom perspective view of the MSC harvesting system of FIGS. 19 and 20 illustrating an MSC collecting apparatus in the form of a syringe operatively connected to the perforated tube.

As more clearly depicted in FIGS. 19, 20 and 21, upon rotational and or linear driving of the perforated tube 304 into the bone, a buttress thread structure 350 extending circumferentially about and along the length of the tube forms a distally facing slope or face 352 and a proximally facing "cliff" 354, (best seen in FIG. 20) which permit either the rotational or linear distal driving of the tube while preventing proximal slipping thereof. The float 328 will abut the cancellous bone thereby compressing the spring 334 while also opening further apertures 306 in the perforated tube as the perforated tube is advanced. The threads may be dual lead. The perforated tube is first advanced up to the bone with a nested trocar/obturator such that the trocar when rotated back and forth removes the cortical bone to expose the underlying cancellous bone. Subsequently, the trocar is removed and the float assembly (including the spring and plug) is placed within the perforated tube. The perforated tube is then driven into the cancellous bone a first distance thereby locating a first amount of cancellous bone within the perforated tube. As shown in FIG. 21, a syringe 280 connected to the perforated tube, e.g., via a collar 282 configured to rotate around a perforated tube longitudinal axis G-G at a selected location intermediate the distal and proximal ends of the perforated tube. The collar further includes a connection portion 283 to interface with a tube 285 extending to the syringe via an intermediary filter 286.

Figure 22:
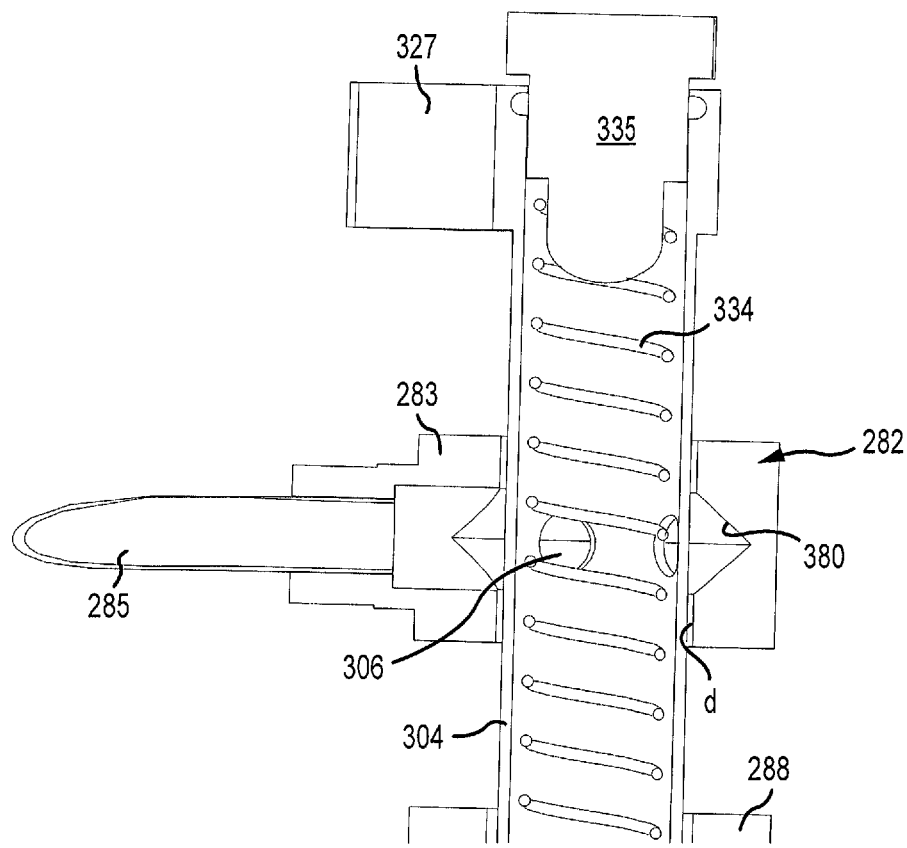
FIG. 22 is a side sectional view of a proximal end portion of the harvesting system of FIG. 19 showing portions of the collar position.

Referring to FIG. 22, elements of, the collar 282 are shown in greater detail. The collar includes a circumferential groove 380 located within the inner diameter d of the collar such that when connected to the perforated tube 304 the array of spaced apart apertures 306 extending through the perforated tube near its proximal end 321 are in fluid communication with the circumferential groove. When suction is applied via the syringe, bone marrow aspirate may travel via the perforated tube's distal end 322 and/or tube perforations 306 proximally through the at least one opening 332 of the float, and further proximally via the array of spaced apart holes and the float body 329 into the collar grove 380 and through the tube connection portion 283 of the collar, through the tube 285 (and optionally through the filter 286) and into the syringe.

Next, the perforated tube 304 is further driven into the cancellous bone a second distance thereby locating a second amount of cancellous bone within the perforated tube and thereby further proximally displacing the float 328 such that further perforations 306 of the tube are opened. Then suction is repeated. This step may be repeated multiple times until the tube is at maximum insertion depth. A concentrically arranged handle 288 may be located along the length of the perforated tube and configured such that a medical person may grasp the concentrically arranged handle with a left hand while rotating the T-handle 327 of the perforated tube in order to permit further control and guidance during placement and advancement. The concentrically arranged handle 288 may have complementary buttress female threads or may be smooth and unthreaded but comprised of a material with a hardness (e.g., durometer) less than the material comprising the male threads. Any of the components may be laser marked or otherwise gradated to permit visual or hepatic feedback to the medical practitioner of amount of advancement of one component relative to the other, which may, in turn, allow the medical user to more accurately determine the amount of cancellous bone disposed within the inner portion of the perforated tube and/or number of perforations open to fluid communication with the bone marrow fluid.

Figure 23:
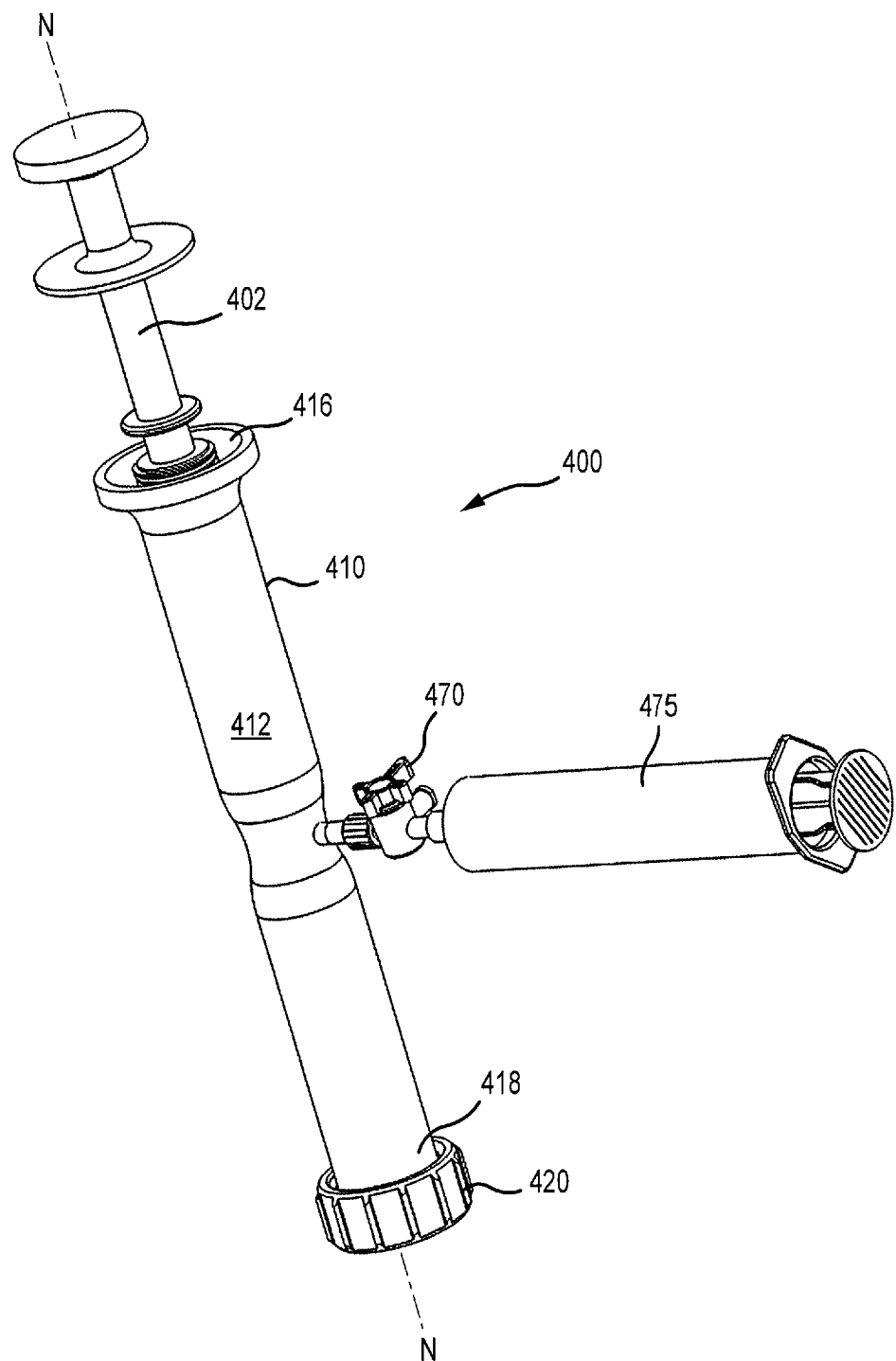
FIG. 23 is a side perspective view of a rinsing apparatus in accordance with an embodiment.
Figure 24:
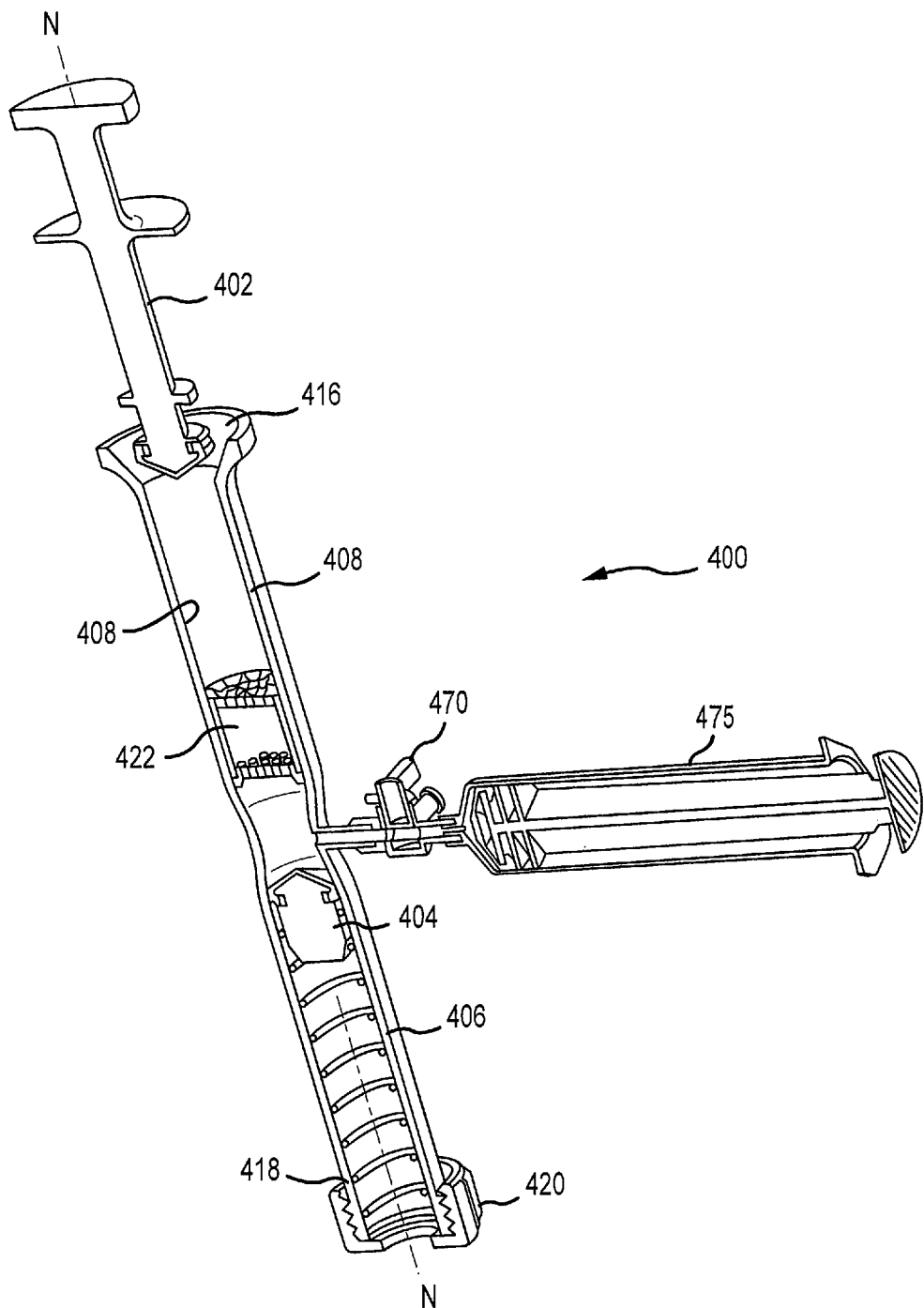
FIG. 24 is a sectional side perspective view of the rinsing apparatus of FIG. 23.
Figure 25:
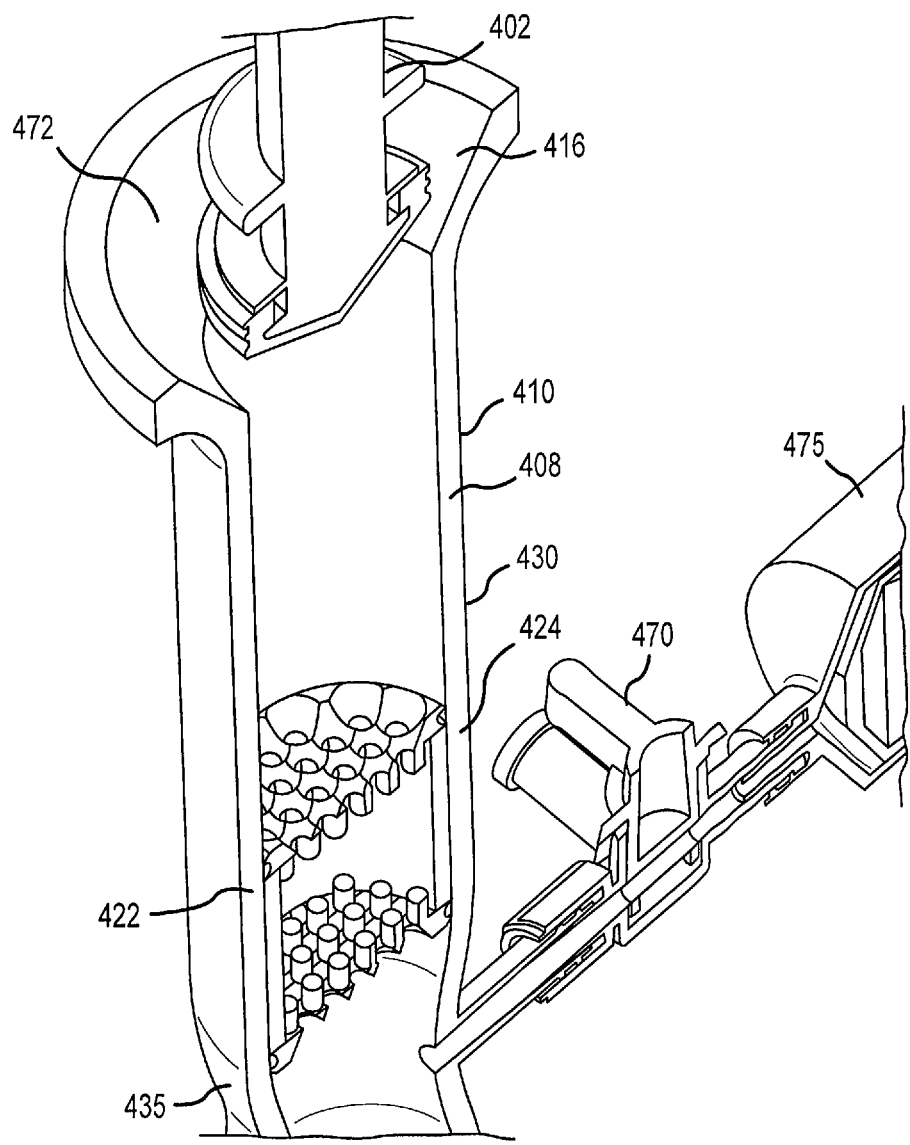
FIG. 25 is an enlarged top sectional perspective view of a portion of the rinsing apparatus of FIG. 23.

In another embodiment as shown in FIGS. 23 and 24, a system 400 for processing harvested bone graft/marrow and bone marrow aspirate includes a hand plunger 402 and a piston 404 biased by a spring 406 reciprocally positioned within an internal cavity 408 formed by a cylindrical body portion 410 formed along and extending circumferentially about the longitudinal axis N-N of a tube 412. A holding chamber 422 configured to at least partially retain the harvested bone graft/bone marrow aspirate is slideably and reciprocally positioned in the internal cavity 408 intermediate the plunger 402 and the piston 404. The tube includes an open proximal end 416 adapted to reciprocally receive the plunger and a distal end 418 which is closed by an end cap 422 threadably secured thereto and structured and arranged to retain the spring 406 in the internal cavity 408 and in contact with the piston 404.

Figure 26:
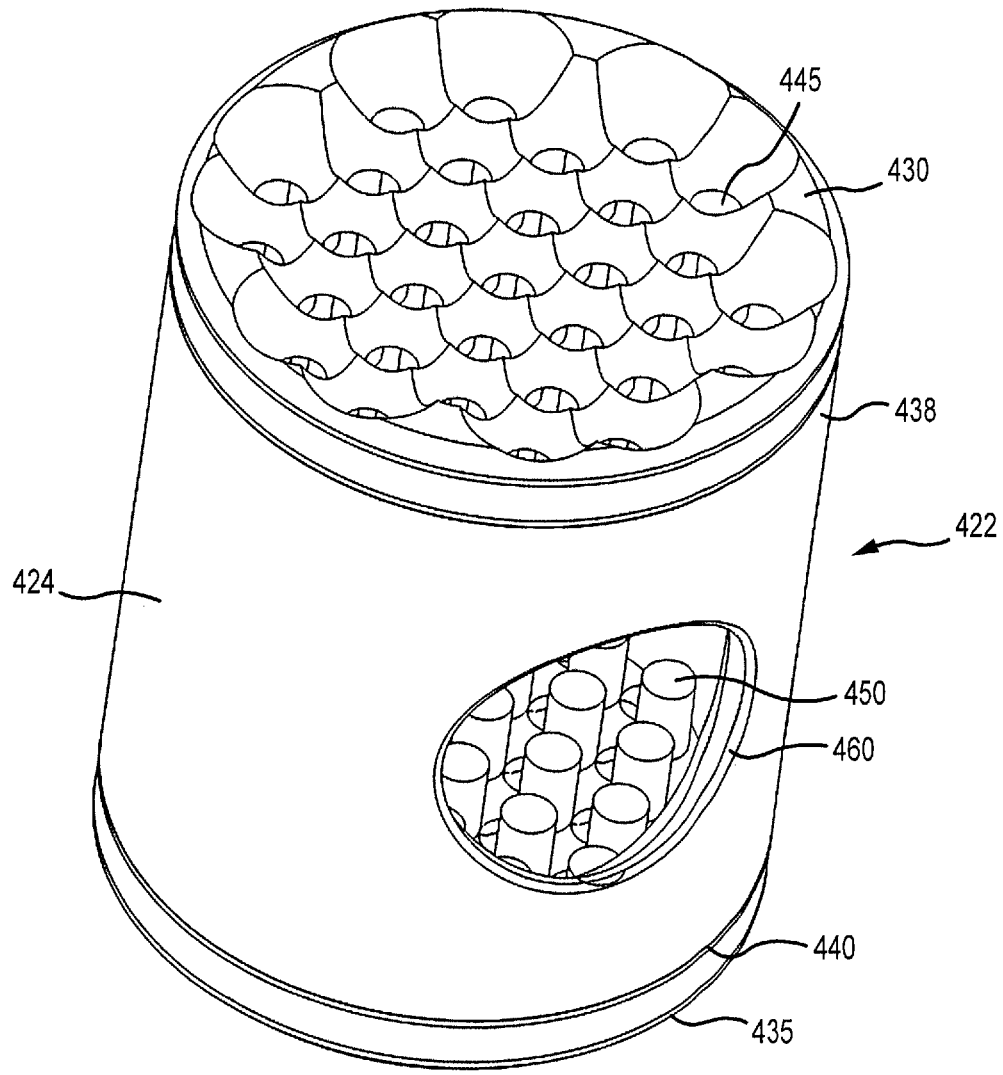
FIG. 26 is a side perspective view of a holding chamber in accordance with an embodiment.

Referring now to FIGS. 25-28, elements of the chamber 422 are shown in greater detail. The chamber includes a cylindrically shaped body portion 424 adapted to fit inside the internal cavity 408 and to slide in both the proximal and distal directions along axis N-N in response to forces exerted thereon by fluids in the cavity and the reciprocating movements of the plunger and the piston. Referring to FIG. 26, the chamber includes oppositely positioned top and bottom end portions or caps 430/435 secured to a respective proximal and distal end 438/440 of the body portion 424, each end portion having a plurality of holes 445 extending therethrough establishing fluid communication between the interior of the holding chamber and the inner portion of the tube. The holding chamber may be at least partially filled with packing material shown at 447 in FIG. 27. The packing material is configured to respond to the washing action caused by the reciprocating piston such that it bombards the bone graft material to dislodge MSC's and/or other components of the harvested bone graft. The packing material may be in the shape of balls, beads, rods, triangular volumes, cubes or irregular shaped masses and may be formed of metals, polymers, ceramics or other materials, e.g., PEEK, titanium, UHMPE, tantalum, silicon nitride, glass or morcellated cortical bone. The holes 445 formed in the end portions 430/435 may be sized in relation to the packing material such that the packing material is generally larger than the holes in order to retain the packing material within the holding chamber.

Figure 27:
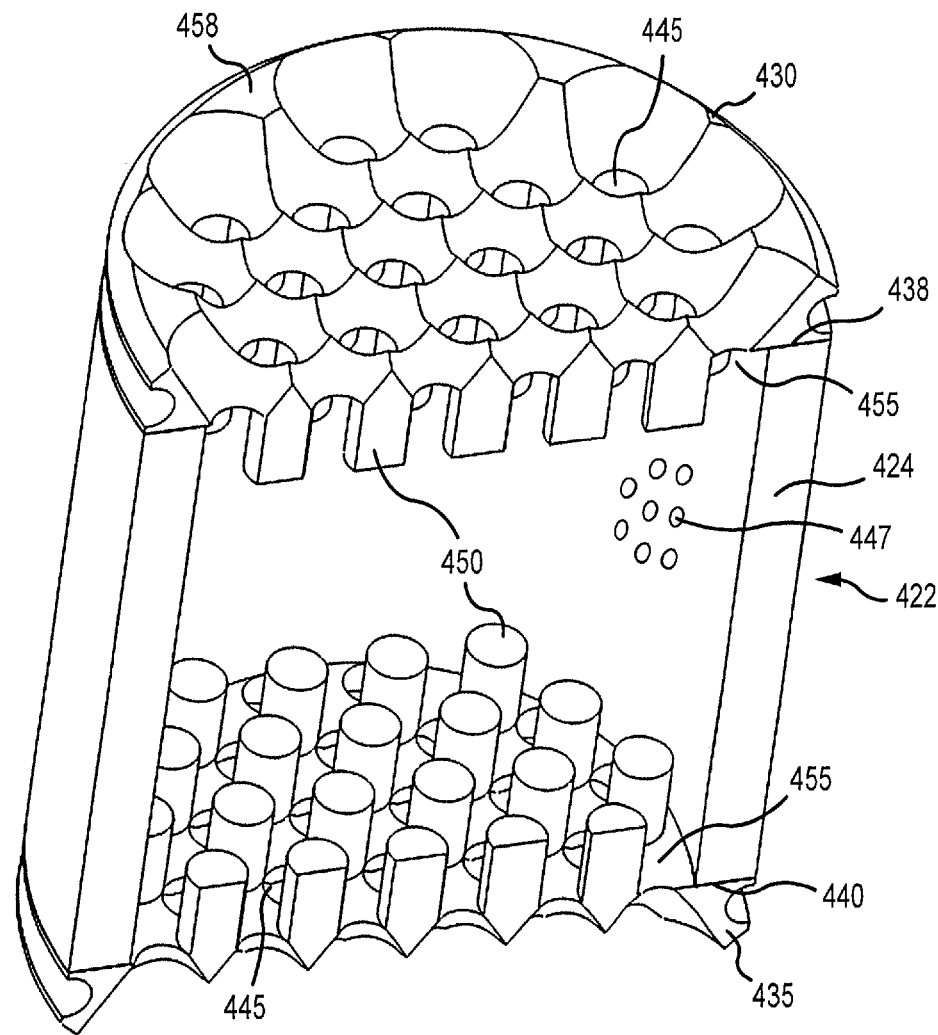
FIG. 27 is a top sectional perspective view of the holding chamber apparatus of FIG. 26.
Figure 28:
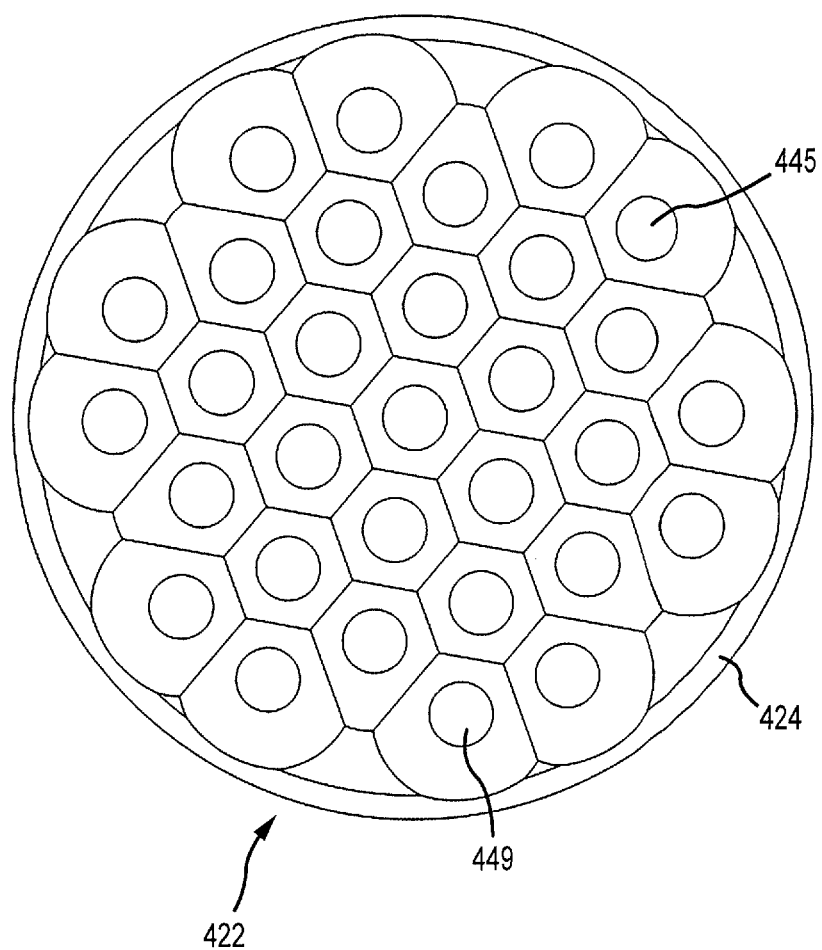
FIG. 28 is a top plan view of the holding chamber apparatus of FIGS. 26 and 27.

As best seen in FIGS. 27 and 28, the holes may include a circular cross-section 449 substantially transverse to their length or may have an elliptical, rectangular, square, diamond, or cross shape cross-section. To prevent clogging of the holes with the packing material, anti-clogging structures, by way of example and not of limitation, protrusions 450 may be located in proximity to the holes to prevent the packing material from obstructing the flow of the fluid through the holding chamber. The protrusions may surround the holes on an inner surface 455 of each of the end portions. Additionally, as shown in FIGS. 26 and 27, each of the plurality of holes may have a cross-section parallel with its length which is variable an outer surface 458 of each of the end caps to the respective inner surfaces, e.g. tapered toward the interior of the holding chamber, thereby effectively creating a nozzle profile such that jetting is created by the movement of the fluid through the holes to further enhance the dislodgement of the MSC's and or other biologic material from the harvested bone marrow. The cylindrically-shaped body 424 may have an access opening 460 adapted to receive the packing material and/or bone marrow. Alternatively, one of the end portions may be removably coupled to the cylindrically-shaped body in order to load the packing material and/or bone marrow.

Figures 29A, 29B, 29C:
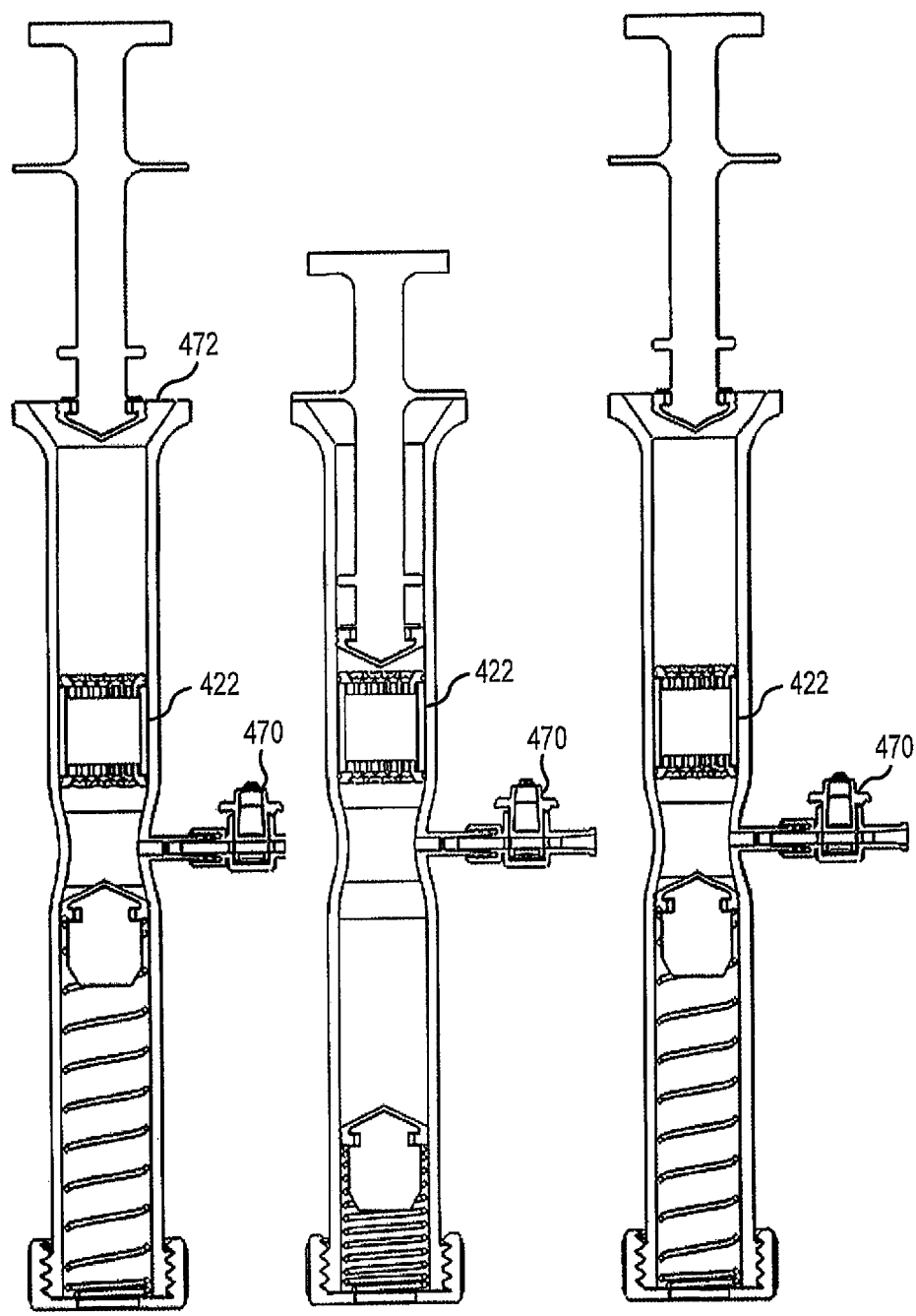
FIG. 29A is a side sectional view of the apparatus of FIG. 23 showing the plunger fully withdrawn.
FIG. 29B is a side sectional view of the apparatus of FIG. 29. A showing the plunger fully inserted.
FIG. 29C is a side sectional view of the apparatus of FIG. 29A showing the plunger returned to the fully withdrawn position.

After packing the holding chamber, it may be inserted into the internal cavity 408 formed by the cylindrical body portion 410 of the tube 412. Bone marrow aspirate may also be injected or otherwise placed within the inner portion of the tube. A stop cock 470 coupled to the tube is switched to the closed condition. The plunger 402 is positioned within the tube via a funnel opening 472 formed in the end 416. As the plunger is displaced distally to force the fluid (e.g., bone marrow aspirate) through the holding chamber and distally towards the distal piston thereby forcing the distal piston distally against the force of a biasing mechanism such as a diaphragm or, in the embodiment shown, the spring 406. Next the plunger is displaced proximally thereby withdrawing it from the tube and creating a suction force on the fluid causing the fluid to flow in a reverse direction. The spring urges the distal piston in the proximate direction in response to the withdrawal of the plunger, thereby causing the distal piston to follow the fluid. The reciprocation is repeated multiple times as needed to sufficiently wash the bone marrow within the holding chamber. These washing cycles are shown in FIGS. 29A, 29B and 29C sequentially.

The reciprocating fluid causes the packing material to cyclically bombard the bone marrow to assist in dislodging the MSC's and other biologic material from the bone marrow. Moreover, as the reciprocating fluid passes through each of the holes, the nozzle shape described above causes jetting of the fluid which further enhances the washing of the bone marrow.

After the multiple reciprocating washing cycles are completed, a syringe 475 is coupled to the tube, and the stop cock 470 is transitioned to an open position. The fluid is then forced into the syringe where it is collected for patient treatment, medical research or other applications, and the holding chamber may be removed to recover the remaining bone marrow for further therapeutic use along with or separate from the wash.

Although the system described above may be designed for ergonomic manually hand powered use, the invention is not so limited, and any number of pneumatic, hydraulic or mechanical actuators may be used in order to more reproducibly control the reciprocating action of the rinsing system. Installing such actuators in the system permit more precise control of certain parameters such as piston velocity, acceleration, displacement and number of strokes and pressure gradient within the system.

For example, according to an embodiment, a mechanically actuated assembly may have pistons which are operably coupled to one another by a linkage assembly to match the timing of each piston's displacement. Alternatively, the pistons may not be operably coupled, and the proximal piston may be mechanically or otherwise actuated (pneumatically or hydraulically) in the distal direction, thereby causing the fluid to displace the distal piston against the force of a biasing mechanism such as a spring, a diaphragm or compressed air. When the proximal piston's direction of movement is reversed such that it moves in the proximal direction, the distal piston may be forced by the biasing mechanism to return to its neutral proximal position.

Figure 30:
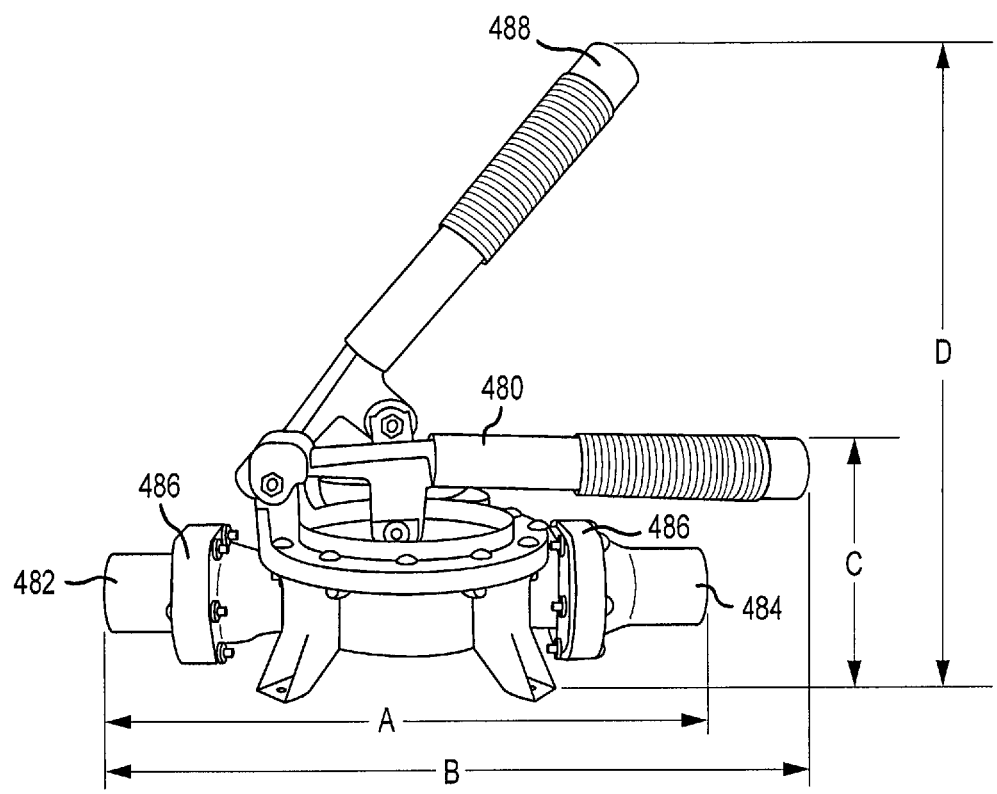
FIG. 30 is a side perspective view of a diaphragm pump in accordance with an embodiment.

According to yet another embodiment the proximal piston may be driven by a hand or a mechanically, hydraulically or electrically actuated diaphragm pump, such as the pump 480 shown in FIG. 30. The proximal end of the tube described above may be coupled to the fluid coupling 482 of the diaphragm and the opposite fluid coupling 484 may be sealed and not used, and the one-way valves 486 may be removed. When an operating handle such as the handle 488 is activated to initiate the pumping action, the fluid may reciprocate in and out of the washer tube to affect the same washing action as hereinabove described in the aforementioned embodiments. Alternatively, the opposite fluid coupling (e.g. inlet) may be operably coupled to the fluid coupling (outlet) via external tubing coupled to one-way valves located outside of the pump to create a closed fluid loop wherein the holding chamber is positioned along the loop in between the inlet and outlet. The pump then forces fluid through the bone marrow in order to wash it.

In yet other embodiments, megasonic frequencies (e.g., 800-2000 kHz) may be used to dislodge MSC's or other biologic material from the harvested bone graft/marrow (or from the wash from the above described systems) without damaging their structure or viability, which may otherwise occur from the random violent cavitation occurring with lower ultrasonic frequencies commonly employed for cleaning tools or for sonicating biologic materials in analytic labs. At the higher megasonic frequencies, acoustic streaming dominates the cleaning process and the cavitation is relatively weak versus the lower ultrasonic frequencies; however, at the megasonic frequencies the number density of bubbles is large and the bubble size small and so the cleaning effects from this weaker gentler cavitation is still significant in part due to the high fluid velocities from the highly directional acoustic streaming and the boundary layer effect where these smaller bubbles are able to clean closer to the substrate surface. As frequency increases, the momentum-transfer boundary layer thickness decreases as square of the frequency. Therefore, at the megasonic frequency range, even sub-micron particles are exposed to the cleaning fluid and chemistry. In some embodiments a very brief exposure to the lower ultrasonic frequencies may assist in removing biologic material from the bone graft substrate via violent cavitation followed by exposure to megasonic frequencies in order to wash via acoustic streaming the biologic material from the substrate.

The system may include a radiofrequency generator and controller in order to drive a piezoceramic transducer located within a vessel holding the bone graft (intact or morcellated). The vessel may be filled with a fluid (comprising, e.g.: saline, citric acid solution, bone marrow aspirate, naturally occurring surfactants derived from the same patient, e.g., phospholipids extracted from the synovial fluid of a joint, e.g. phosphatidyl choline. These extracts and their components have been shown to be surface active in reducing the surface tension of water which may assist in the washing and which may be diffused with oxygen gas. The increased gas within the fluid, in contrast to ultrasonic cleaning which usually employs a degassed fluid, actually improves the particle removal efficiency while employing megasonic frequencies.

Various frequencies within or near the megasonic range may be employed at the transducer's respective resonant frequency, and even employing lower trans-sonic frequencies between 400-600 kHz may provide sufficient precleaning of the substrate with lower likelihood of cell damage prior to employing the higher megasonic frequencies, e.g., frequency sweeping at 470 kHz may be useful. According to particular embodiments, acoustic power levels of approximately 10 W/cm2 may be used but this may range from about 2-30 W/cm2.

Exemplary Methods

In application, the aforementioned MSC harvesting apparatus may be advantageously employed by the medical practitioner to efficiently and quickly obtain and process autologous fluids containing a high MSC concentration for therapeutic treatment of a patient's condition in compliance with current FDA regulations. Exemplary process steps include the following:

1. Selecting a location in the patient's skeletal system for harvesting the patient's MSC's;
2. Creating an aperture extending through an outer layer of the skeletal system formed by the cortical bone into cancellous bone located in an internal cavity at the preselected location in the patient's skeletal system with an elongate perforating device, the perforating device having a body member extending along and circumferentially about a longitudinal axis thereof and a cannula movably positioned thereon and extending along the longitudinal axis;
3. Positioning the cannula on the aperture, the cannula being structured and arranged to removably receive an aspiration device;
4. Withdrawing the elongate perforating device from the aperture and cannula;
5. Inserting an aspiration device through the cannula into at least one area within the internal cavity;
6. Obtaining at least one sample or plug of cancellous bone (bone plug) from the at least one area within the internal cavity;
7. Withdrawing the aspiration device from the internal cavity and the cannula;
8. Placing one of the at least one bone plugs into an aspiration device and inserting the aspiration device through the cannula into at least one area within the internal cavity;
9. Aspirating at least one sample of the patient's bone marrow blood and MSC's through the bone plug in the aspirating device;
10. Removing the bone plug from the aspirating device;
11. Inserting the bone plug into a filtering apparatus;
12. Flushing the bone plug in the filtering apparatus with the at least one sample of the patient's bone marrow blood and MSC's;
13. Collecting the autologous media after it is flushed through the bone plug;
14. Centrifuging the autologous media to separate and concentrate the MSC's; and
15. Collecting the concentrated MSC's.

Following collection of the concentrated MSC's, they may be reinjected into the patient at a specific treatment site as needed to treat the specific conditions of which the patient complains, for example the treatment of pain, degeneration, inflammation, and to expedite post-operative healing among others. The concentrated MSC's may also be injected intravenously into the patient for general therapeutic treatment and/or added to creams, ointments or salves for application to a patient's skin for treatment of dermatological and cosmetic conditions.

In another embodiment of the instant invention, an infiltrating medium, MSC's and physiological fluid may be infused into a cavity formed in a patient's skeletal system under closely controlled pressure. Systemic treatment of a patient may be achieved without intravenous injection by first washing the bone marrow internally with the physiologic solution using a high pressure system and forcing the MSCs in the bone marrow into the patient's circulatory system. The entire process occurs within the patient.

While the foregoing outline of the methodologies of the present invention for harvesting MSC is presented in detail, it is to be understood that alternative approaches of varying complexity may also be taken without departing from the scope of the invention. For example, in its simplest form, a method for harvesting a patient's mesenchymal stem cells includes inserting a Jamshidi-type needle or stylet having a preselected diameter or size and a cannula through the cortical bone at a preselected location on a patient's skeletal system forming an aperture therein, removing the stylet, advancing the cannula into the patient's bone marrow and aspirating bone marrow material, blood, MSC and MSC-like cells through a cancellous bone plug positioned in the cannula, whereby harvested MSC cell count is increased.

In another embodiment, a cannula used in conjunction with a Jamshidi-type needle has external or male threads formed on an end thereof, the threaded end of the cannula being adapted to be controllably threaded into and/or withdrawn from an aperture formed in a patient's cortical bone.

In still another embodiment, a larger diameter Jamshidi needle or stylet is movably deployed within an outer cannula having at least one externally-threaded end, the needle being adapted to create an aperture in the patient's cortical bone structure so that once the sharp tip penetrates the cortical bone, the inner stylet—trocar is removed, the tip of the cannula is threaded into the cortical bone to maintain its position, following which an inner cannula with multiple apertures is advanced into the marrow bone obtaining a bone plug and aspirating marrow blood through the bone plug as the cannula is advanced or retracted. The inner cannula may be threaded such that it is advanced or retracted through the outer cannula in a more controlled fashion during aspiration.

In still another embodiment, the aspirant contains red blood cells and/or platelets, and the harvesting method may include the additional steps of lysing the red blood cells and/or the platelets.

The flushing medium may comprise, by way of example and not of limitation, autologous fluids collected from the patient including bone marrow, cancellous bone and bone marrow blood, MSC's, bone marrow aspirate plasma (BMAP), bone marrow aspirate serum, peripheral blood plasma, peripheral blood serum or a combination thereof. It may also include other physiologic fluids such as heparin, acid citrate dextrose anticoagulant solution, buffered saline solution or a combination thereof. Optionally, the cancellous bone plug may be ground via mechanical means prior to flushing, thereby homogenizing the cancellous bone to increase fluid access to the trabecular cavities formed therein. These cavities are rich repositories of MSC.

Experimental Protocol and Verification of Results

The research investigations conducted in the course of development of the system and methods of the instant invention followed the protocols for the identification of human MSC's set forth by M. Dominici et al. in their position paper published by The International Society for Cellular Therapy entitled, Minimal Criteria for Defining Multipotent Mesenchymal Stromal Cells, Cryrotherapy (2006), Vol. 8, No. 4, pp. 315-317. Dominici et al. define three criteria for the definition of MSC's:

1. MSC's must be plastic-adherent when maintained in standard culture conditions;
2. MSC's must be positive for surface antigens CD73, CD90 and CD105 (at least 95% of the population) and negative for CD45, CD34, CD14 or CD11b, CD79α or CD19 and HLA-DR (less than 2% of the population); and
3. MSC's must be able to differentiate into osteoblasts (bone cells), adipocytes (fat cells) or chondroblasts (cartilage cells).

The cell differential may be identified by the use of appropriate stains. For example, osteoblasts may be identified by staining with Alizarin Red or von Kossa staining; adipocytes by staining with Oil Red O; and chondroblasts by staining with Alcian blue or immunohistochemical staining for collagen type 11.

Figure 31:
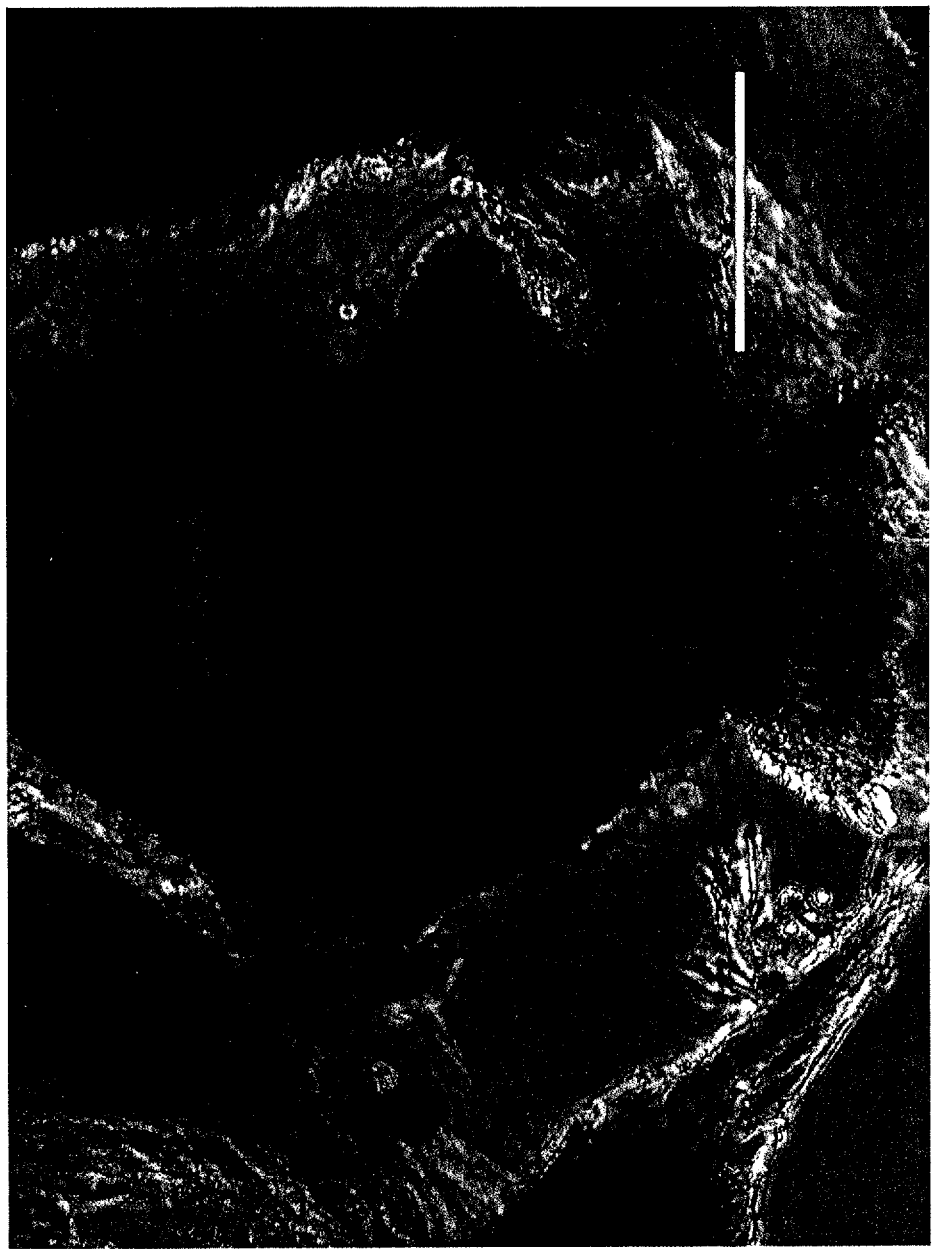
FIG. 31 is a photomicrograph of a GAG-rich matrix within sections of trabecular cavities in a cancellous cavity formed in a patient's skeletal structure.

FIG. 31 illustrates an image of an area within a cavity formed by the cortical bone in the skeletal structure of a patient from which MSC's were collected in accordance with embodiments of the present invention. The bone portion stains red with Alizarin Red and the glycosaminoglycan (GAG)-rich matrix within sections of trabecular cavities are stained blue with Alcian Blue. Obtained samples were processed mechanically and enzymatically.

All of the above-referenced criteria to qualify the cells as MSC's were met in performing all of the methods herein described, namely: drawing aspirate through the bone core, mechanically extracting the GAG region of the bone core and enzymatic processing of the GAG-region of the bone core.

Figure 32:
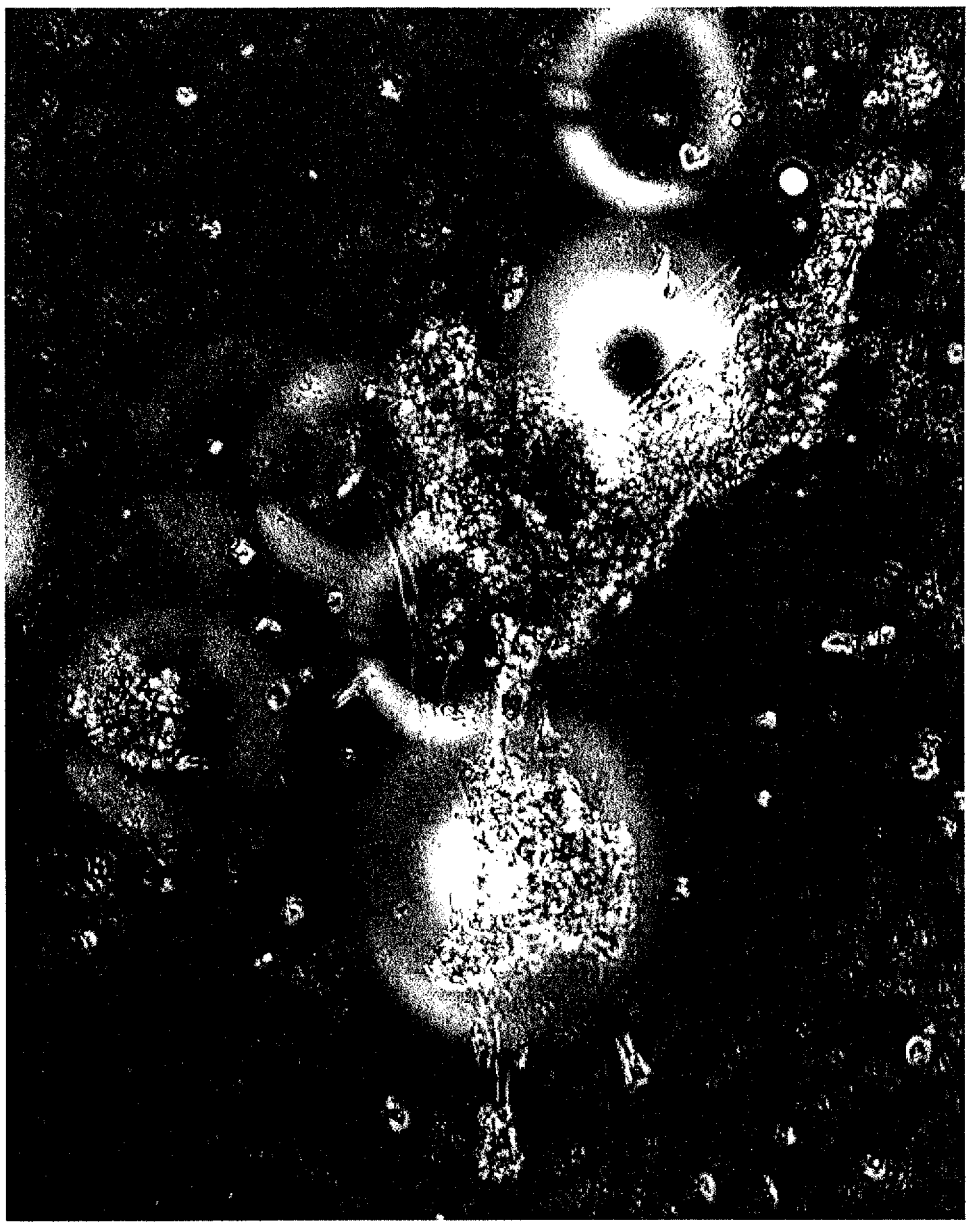
FIG. 32 is a photomicrograph of MSCs in a GAG-rich matrix such as shown in FIG. 31.

Referring now to FIG. 32, as shown in greater detail, regions of the bone core rich in glycosaminoglycans (GAG) are the regions of the trabecular bone which harbor the mesenchymal stem cell populations. The feathery, darker stained regions are the regions from which MSC's are collected in accordance with the methods of the present invention. This is evident via the colony forming unit (CFU) and flow cytometry data collected using enzymatic (collagenase) and mechanical digestion methods. In this respect, the cells yielded from the enzymatic digest reflect the mesenchymal cell population harvested in the mechanical method, as the starting material was identical, and the only difference was the reduction of the matrix to a particulate which released the resident cell population into suspension. Similarly, the mechanically derived GAG-rich region houses the exact same cell content but retains them in an autologous biologic scaffold and is ideal for cell therapy delivery and maintaining cellular viability (lack of adhesion of an MSC results in cell death). Most prior art cell therapies lack a biological scaffold (here an autologous scaffold is offered) and are known to result in diminished outcomes therefore and applicable biologic or synthetic scaffolds are highly sought after. The methods herein disclosed collect concentrated mesenchymal stems cells already attached to an ideal biological scaffold.

As noted above, the process involved to remove the GAG-rich matrix from the calcified bone may include mechanical and/or enzymatic (collagenase) processes. After collection, the bone core (as described) may be processed via mincing, homogenization, micronization or ultrasonication. Before, concurrently or following this processing step, the bone core can be rinsed with an anti-coagulant, biological serum plasma, hypotonic solution or enzymatic suspension. The GAG-rich particles resulting from mechanical processing are between 40-500 microns.

On average, a typical bone core/dowel had a total wet (freshly harvested) weight of approximately 60-70 milligrams (this is not the GAG-rich region separated from the calcified bone; it represents the bone core in total). With respect to material volume, this is approximately 60-70 μl worth of an equivalent aqueous-based material. This is the weight/volume of the raw bone core material. When mechanically processed, the resulting GAG-rich, MSC containing matrix can be placed in any fluid volume desired.

By contrast, at minimum, commercially available kits process 60 mL of bone marrow aspirate (BMA), which is equivalent to 60 grams. This is approximately 1000× more starting material than the bone core used in the methods of the present invention. This bone marrow aspirate is usually processed to produce a concentrated buffy coat layer which is in a volume of approximately 3-5 mLs of final product known as "bone marrow aspirate concentrate" or, "BMAC".

Figure 33:
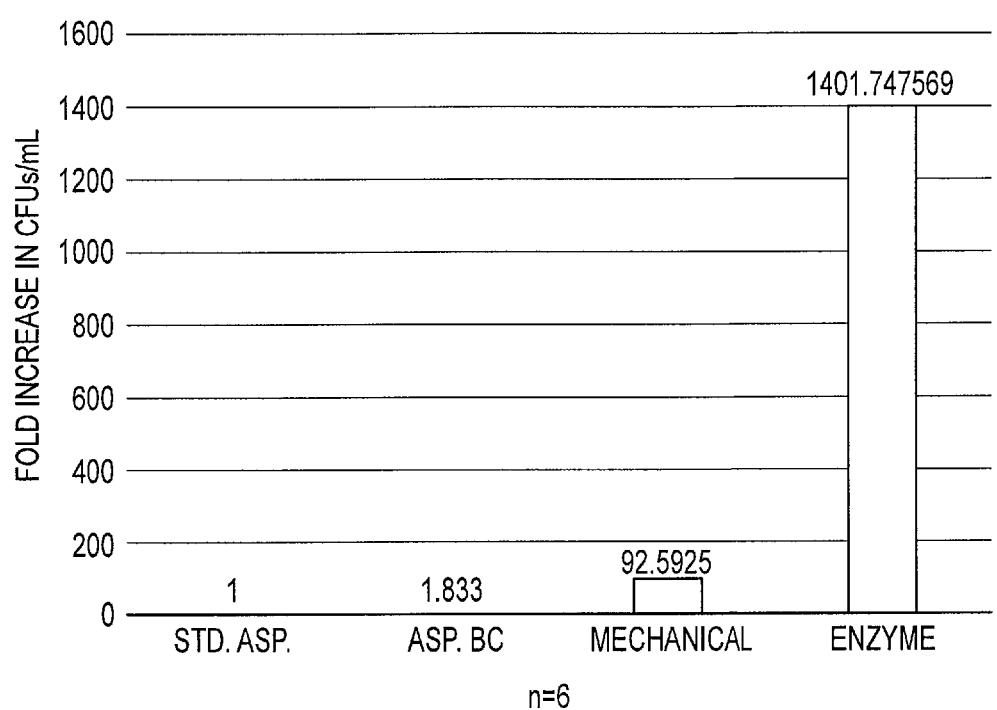
FIG. 33 is a bar graph showing the increase in CFU count compared to bone marrow aspirate concentrate obtained using standard aspiration methods.

In accordance with the methods herein disclosed, bone cores were processed using mechanical homogenization and enzymatic (collagenase) digestion (in parallel, not in series). All treatments included the processing of up to 60-70 mg of bone core. The resulting products were cultured and compared to 500 µl of bone marrow aspirate concentrate products. On average, we find via enzymatic digestion that the GAG-rich region of the bone core contains ~200× more colony forming units (CFUs) than the standard bone marrow aspirate counterpart. This is accomplished with 1000× less starting volume in starting material. These results are reflected in the bar graph shown in FIG. 33.

Figure 35B:
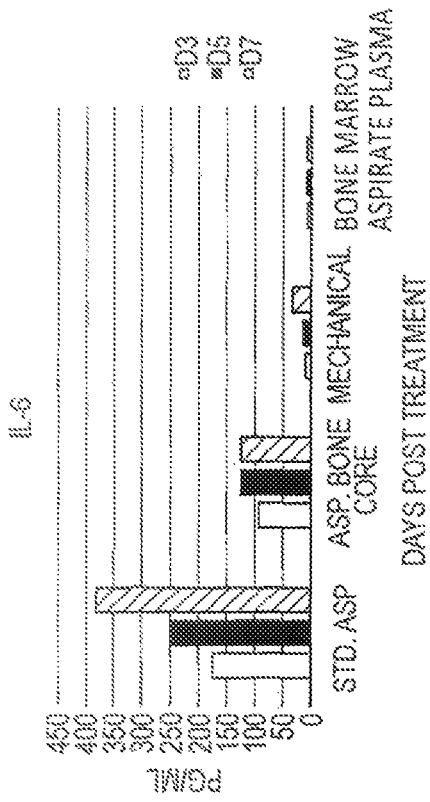
FIG. 35B is a bar graph illustrating the retention of another non-inflammatory phenotype post extraction using different harvesting methodologies.
Figure 35C:
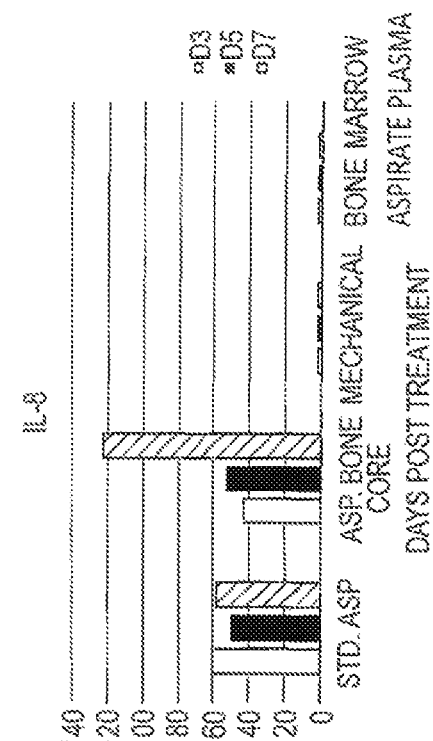
FIG. 35C is a bar graph illustrating the retention of yet another non-inflammatory phenotype post extraction using different harvesting methodologies.
Figure 35A:
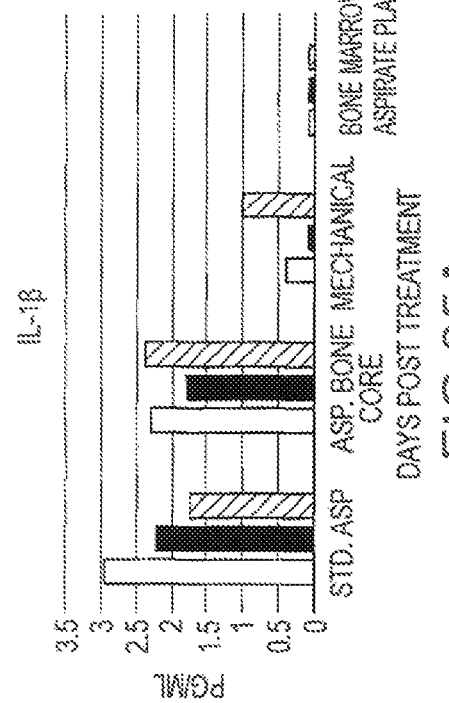
FIG. 35A is a bar graph illustrating the retention of a non-inflammatory phenotype post extraction using different harvesting methodologies.

Washing the bone core and processing the GAG-rich fraction (blue stained region in FIG. 31) yields 3 distinct MSC subpopulations recognized in the literature: LepR MSCs, CXCL12 Abundant Reticular Cells (CAR MSCs) and Nestin-expressing MSCs. This is evident by the increase expression of these factors in our MSC populations harvested compared to a BMAC from a standard aspirate. These results are shown in FIGS. 34A, 34B and 34C. Further, the analysis showed that the MSCs when still associated with the GAG-rich region (mechanical processing has all the GAG-rich regions present with the MSCs still attached) they are resistant inflammatory signals (TNF-alpha added to media) and do not promote inflammatory processes. Therapeutically, this is crucial to ensure the MSCs do not promote the disease. Therefore the MSC produced using the herein described processes has an associated autologous bio-matrix (GAG-rich regions) which assists in MSCs retaining a non-inflammatory phenotype. This is shown in FIGS. 35A, 35B and 35C. It is believed that drawing the bone marrow aspirate through the core and washing the core all result in MSC collection via shearing them off of the GAG-rich region of the bone core. This is verified by the increase of MSCs collected from mechanical and enzymatic digestion of this GAG-rich region.

Changes may be made in the above methods and systems without departing from the scope hereof. It should thus be noted that the matter contained in the above description and/or shown in the accompanying figures should be interpreted as illustrative and not in a limiting sense. The following claims are intended to cover all generic and specific features described herein, as well as all statements of the scope of the present methods and apparatus, which, as a matter of language, might be said to fail there between.

What is claimed is:

1. A method of preparing a therapeutic solution for administration to a patient or client for treatment or for medical research, the therapeutic solution comprising a micronized autologous biologic scaffold and autologous mesenchymal stem cells (MSCs), the method comprising:
    (a) receiving a fluid into a chamber, the chamber not being in fluid communication with the patient or client;
    (b) receiving an autologous cancellous bone plug or core into the chamber, the autologous cancellous bone plug or core including autologous calcified bone, trabecular cavities, MSCs and a glycosaminoglycan-rich (GAG-rich) matrix;
    (c) mechanically producing the therapeutic solution without the use of an enzymatic digestion by causing at least a portion of the GAG-rich matrix to separate from the calcified bone and trabecular cavities and further be broken mechanically into micronized autologous biologic GAG-rich matrix scaffold particles within the chamber by non-enzymatic processing such that at least a portion of the autologous MSCs remain attached to the micronized autologous biologic GAG-rich matrix scaffold particles in solution with the fluid and wherein the at least a portion of the autologous MSCs retain an anti-inflammatory phenotype following the non-enzymatic processing; and
    (d) providing the therapeutic solution comprising the fluid, the micronized autologous biologic GAG-rich matrix scaffold particles and the at least a portion of the autologous MSCs for extraction from the chamber, wherein the therapeutic solution has a reduced concentration of calcified bone as compared to cancellous bone plug or core.

2. The method of claim 1, wherein the therapeutic solution comprises micronized autologous biologic GAG-rich matrix scaffold particles having a size of about 40-500 microns.

3. The method of claim 1, wherein the at least a portion of the autologous MSCs comprise at least three distinct MSC subpopulations including: LepR MSCs, CXCL 12 Abundant Reticular Cells and Nestin-expressing MSCs.

4. The method of claim 1, further comprising (e) discarding at least a portiion of the searated calcified bone as a waste product.

* * * * *

UNITED STATES PATENT AND TRADEMARK OFFICE
CERTIFICATE OF CORRECTION

| | |
|---|---|
| PATENT NO. | : 11,655,454 B1 |
| APPLICATION NO. | : 15/933314 |
| DATED | : May 23, 2023 |
| INVENTOR(S) | : Edward Jeffrey Donner et al. |

It is certified that error appears in the above-identified patent and that said Letters Patent is hereby corrected as shown below:

On the Title Page

Column 2, ABSTRACT should read:
A mesenchymal stem cell harvesting system and method for increasing the efficiency of collecting and processing physiological fluids containing mesenchymal stem cells from a cavity within a patient's skeletal system. Microenvironments rich in MSC production and concentration within a cavity, for example the patient's ilium, are penetrated with a pointed instrument used to create an aperture in the hard cortical bone forming the cavity followed by the insertion of an aspiration device which extracts one or more samples of cancellous bone, bone marrow, bone marrow blood and other aspirated material. The aspirate is rinsed and may be filtered to remove unwanted material and to increase the concentration and purity of the mesenchymal stem cells in the aspirant far beyond levels formerly obtainable for use in autologous treatment of the patient.

Signed and Sealed this
Eighteenth Day of July, 2023

Katherine Kelly Vidal
*Director of the United States Patent and Trademark Office*